United States Patent
Kanand et al.

[11] Patent Number: 6,166,265
[45] Date of Patent: Dec. 26, 2000

[54] PROCESSES FOR THE PREPARATION OF N-BUTYRALDEHYDE, N-BUTANOL AND MIXTURES THEREOF

[75] Inventors: Jürgen Kanand; Rocco Paciello, both of Bad Dürkheim; Michael Röper, Wachenheim, all of Germany

[73] Assignee: BASF Aktiengesellschaft, Ludwigshafen, Germany

[21] Appl. No.: 09/381,452

[22] PCT Filed: Mar. 6, 1998

[86] PCT No.: PCT/EP98/01324

§ 371 Date: Sep. 15, 1999

§ 102(e) Date: Sep. 15, 1999

[87] PCT Pub. No.: WO98/41494

PCT Pub. Date: Sep. 24, 1998

[30] Foreign Application Priority Data

Mar. 17, 1997 [DE] Germany ............... 197 10 994

[51] Int. Cl.⁷ .................................................. C07C 47/02
[52] U.S. Cl. .................. 568/487; 568/449; 568/450; 568/489; 568/491; 568/904
[58] Field of Search ................. 568/449, 450, 568/487, 489, 491, 904

[56] References Cited

U.S. PATENT DOCUMENTS

| 2,922,822 | 1/1960 | Beach et al. .............. 260/614 |
| 4,310,709 | 1/1982 | Rebafka et al. ............ 568/687 |
| 5,705,707 | 1/1998 | Kanand et al. ............ 568/487 |

OTHER PUBLICATIONS

Chang, Journal of Organometallic Chemistry, 492, pp. 31–34, 1995.

*Primary Examiner*—Sreeni Padmanabhan
*Attorney, Agent, or Firm*—John H. Shurtleff

[57] ABSTRACT

Process for the preparation of n-butyraldehyde and/or n-butanol, wherein a) 1,3-Butadiene or a butadiene-containing hydrocarbon mixture is reacted with an alcohol of the formula I $$ROH \qquad \qquad I,$$

where R is $C_2$–$C_{20}$-alkyl or alkenyl which is unsubstituted or substituted by 1 or 2 $C_1$–$C_{10}$-alkoxy or hydroxyl groups, or is $C_6$–$C_{10}$-aryl, $C_7$–$C_{11}$-aralkyl or methyl, at elevated temperatures and superatmospheric pressure in the presence of a Brönsted acid or in the presence of a complex of an element of Group Ia, VIIA or VIIIA of the Periodic Table of Elements with phosphorus- or nitrogen-containing ligands to give a mixture of the adducts of the formulae II

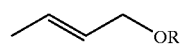

II and III

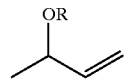

III b) the adduct III is isomerized to the adduct II,
c) the adduct II is converted into the acetal of the formula IV

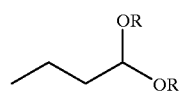

IV d) n-butyraldehyde and/or n-butanol are then produced from this acetal IV by reacting it, in the liquid phase, with hydrogen and water or water in the presence of a homogeneous or heterogeneous transition metal catalyst which differs from dicobaltoctacarbonyl or hydridocobalttetracarbonyl.

24 Claims, 1 Drawing Sheet

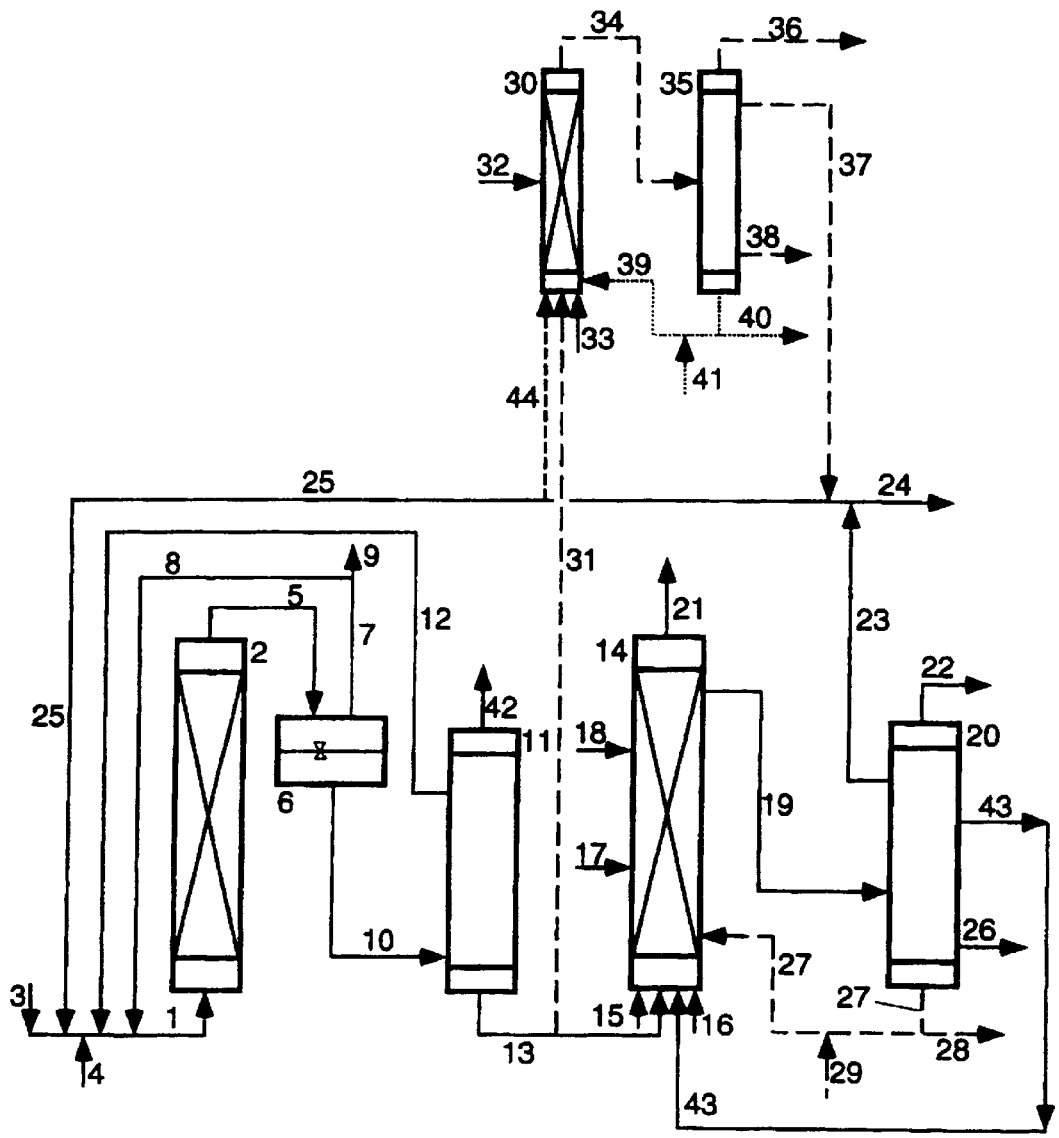

PROCESSES FOR THE PREPARATION OF N-BUTYRALDEHYDE, N-BUTANOL AND MIXTURES THEREOF

This is the U.S. national stage application of PCT/EP98/ 01324 filed Mar. 6, 1998.

The present invention relates to a process for the preparation of n-butyraldehyde and/or n-butanol.

n-Butyraldehyde and n-butanol are major products of the chemical industry and are widely used. n-Butyraldehyde, for example, is produced worldwide in amounts of more than 4 million metric tons/year and is used, inter alia, as a starting material for the preparation of plasticizer alcohols. n-Butanol is used in large amounts as solvent, for example for coatings.

Today, n-butyraldehyde is produced on a large industrial scale virtually exclusively by hydroformylation of propene, using various processes which essentially employ cobalt or rhodium hydroformylation catalysts (Kirk-Othmer: Encyclopedia of Chemical Technology, 4th edition, Volum 4, pages 741–746, John Wiley & Sons, New York 1992).

n-Butanol is one of the most important secondary products of n-butyraldehyde in terms of quantity and is obtained therefrom by hydrogenation. Other processes for the preparation of n-butanol, such as the hydrogenation of crotonaldehyde, which in turn is produced by aldol condensation of acetaldehyde, are now only of historical interest or, like the microbiological production of n-butanol by the fermentation of molasses, are only of regional importance (Kirk-Othmer: Encyclopedia of Chemical Technology, 4th edition, Volume 4, pages 694–696, John Wiley & Sons, New York 1992). These processes, in particular the hydroformylation of propene, require high capital costs, for example for the erection of high-pressure plants for the cobalt-catalyzed hydroformylation or for the purchase of the expensive rhodium catalyst, the installations for handling it in the hydroformylation and for working up spent rhodium-containing catalyst solutions. Furthermore, the preparation of n-butyraldehyde by the hydroformylation process requires synthesis gas plants which deliver the synthesis gas required for the hydroformylation. A further disadvantage of the hydroformylation process is the large amount of the byproduct isobutyraldehyde which is inevitably produced and is of little commercial value because it can be further used only in limited amounts.

1,3-Butadiene is a base chemical which is produced in large amounts in steam crackers and is isolated from the $C_4$ cut of the steam cracker by extraction, for example by means of N-methylpyrrolidone. 1,3-Butadiene is available in large amounts and is a very economical raw material. The preparation of butanol and/or of butyraldehyde starting from the raw material 1,3-butadiene does however entail a number of difficulties. This is due both to the tendency of the 1,3-butadiene to undergo dimerization and polymerization reactions and to the formation of mixtures of 1,2- and 1,4-adducts in the addition reactions. The cause of this chemical behavior is the presence of two conjugated double bonds in the 1,3-butadiene molecule (Kirk-Othmer: Encyclopedia of Chemical Technology, 4th edition, Volume 4, pages 676–683, John Wiley & Sons, New York 1992).

U.S. Pat. No. 2,922,822 and DE-A 2 550 902 disclose that alcohols in the liquid phase react with 1,3-butadiene in the presence of acidic ion exchangers to give the corresponding unsaturated ethers. In U.S. Pat. No. 2,922,822, this reaction is carried out in the presence of a large excess of methanol, which leads to increased formation of the undesirable dimethyl ether. In the process of DE-A 2 550 902, vinylcyclohexene is formed as the main product in this reaction. According to EP-A 25240, the addition reaction of alcohols with 1,3-butadiene is advantageously carried out in the presence of a polar, aprotic solvent, which then has to be distilled off again. According to GB-A 943160, the addition reaction of alcohols is carried out using Brönsted acids in the presence of copper salts.

Futhermore, transition metal complexes having phosphine ligands were used as catalysts for the addition reaction of alcohols with 1,3-butadiene. Chauvin et al. (Bull. Chim. Soc. France (1974), 652) investigated the addition reaction of alcohols with 1,3-butadiene using trialkyl- and triarylphosphine complexes of nickel and of palladium. In some of these reactions, alcoholates, in particular phenolates, were used as cocatalysts. According to DD-A 206989, alkylpalladium(II) complexes with trialkyl- or triarylphosphine or trialkyl or triaryl phosphite ligands are used, in the presence of alkali metal alcoholates, for the reaction of isoprene with alcohols. Kawazura et al. (J. Chem. Soc. Chem. Com. (1972) 2213) use rhodium(III) chloride as a catalyst, as does Dewhirst (J. Org. Chem. 32, (1967) 1297). Taylor (Symposium on new Routes to new Olefins; Division of Petroleum Chemistry, Inc.; American Chemical Society, Boston Meeting, 1972) investigated the addition reaction of alcohols with 1,3-butadiene by means of copper(I) chloride and rhodium(I)-alkadiene complexes. Jolly et al. (Synthesis (1990) 771) mention the reaction of 1,3-butadiene with trialkylphosphine-palladium complexes. In all the reactions stated, mixtures of 3-alkoxybut-1-enes and 1-alkoxybut-2-enes form. In many of these prior art reactions, the conversions and yields are unsatisfactory and said reactions give a large number of oligomeric butadiene derivatives, for which there is virtually no use or which are used only in such small amounts that the major part of these byproducts inevitably formed in a large scale industrial process would have to be disposed of.

U.S. Pat. No. 4,788,325 and Chang (J. Organomet. Chem. 31 (1995), 492) describe the reaction of allyl ethers with alcohols in the presence of hydrogen and carbon monoxide using dicobaltoctacarbonyl ($Co_2(CO)_8$) as a catalyst. Under these conditions, the dicobaltoctacarbonyl is converted into hydridocobalttetracarbonyl ($HCo(CO)_4$), which is the actual catalytically active species. In this reaction, the corresponding saturated acetals are obtained. Chang furthermore describes the hydrolysis of these acetals in the presence of the abovementioned cobalt carbonyls to give the corresponding aldehydes. The disadvantage of this process is that the cobalt carbonyls also act as aldolization catalysts in the hydrolysis, leading to the formation of undesirable aldolization byproducts in the hydrolysis of the acetals. A further disadvantage is that the cobalt carbonyl compounds used are relatively readily volatile and are partly discharged with the aldehyde or alcohol when the product mixture is worked up by distillation, so that, before it is further used, said aldehyde or alcohol must be freed from cobalt carbonyls contained therein by an extensive cobalt removal stage. This process is therefore uneconomical.

U.S. Pat. No. 4,658,069 relates to a process for converting allyl ethers which additionally contain a formyl or carboxyl group into the corresponding diacetals, the allyl ether being reacted with an alkanol under anhydrous conditions and the water formed in this reaction then being removed in a first stage and, in a second stage, the allyl ether acetal obtained in the first stage being converted with the aid of a ruthenium halide catalyst and an alkanol into the saturated diacetal. Iridium halides are also mentioned as suitable catalysts. Under the reaction conditions stated in this patent, only the saturated acetals are formed.

JP-A 25114/1972 relates to a process for the preparation of acetals from allyl ethers by reacting the latter with an alkanol in the presence of a ruthenium(III) chloride catalyst. In the example of this application, 1-methoxy-2,7-octadiene is reacted with methanol and by means of $RuCl_3$ under a nitrogen atmosphere to give 1,1-dimethoxyoct-7-ene. In a further stage, the double bond is hydrogenated over a palladium catalyst and then, in a third stage, the caprylaldehyde dimethyl acetal thus obtained is hydrolyzed with sulfuric acid to give caprylaldehyde.

WO 95/19334 relates to a process for the preparation of butyraldehyde and/or butanol, an alkanol being subjected to an addition reaction with 1,3-butadiene and the resulting allyl ether then being isomerized to the enol ether and being converted into butyraldehyde and/or butanol by reaction with water or water and hydrogen.

It is an object of the present invention to provide an economical process, which can be used on a large industrial scale, for the preparation of n-butyraldehyde and/or n-butanol starting from the raw material 1,3-butadiene, which makes it possible to prepare these products with high yield and selectivity; in particular, the amount of byproducts formed in the process should be small or these byproducts should themselves be desirable commercial products. Furthermore, the process should be flexible to permit the preparation of, alternatively, n-butyraldehyde and/or n-butanol depending on the demand for these compounds. The operation of the process should not be dependent on the presence of a synthesis gas plant and should manage without high-pressure plants or additional purification stages, for example a cobalt removal stage.

We have found that this object is achieved by a process for the preparation of n-butyraldehyde and/or n-butanol, wherein a) 1,3-butadiene or a butadiene-containing hydrocarbon mixture is reacted with an alcohol of the formula I

ROH                                      I, where R is $C_2$–$C_{20}$-alkyl or alkenyl which is unsubstituted or substituted by 1 or 2 $C_1$–$C_{10}$-alkoxy or hydroxyl groups, or is $C_6$–$C_{10}$-aryl, $C_7$–$C_{11}$-aralkyl or methyl, at elevated temperatures and superatmospheric pressure in the presence of a Brönsted acid or in the presence of a complex of an element of Group Ia [sic], VIIA or VIIIA of the Periodic Table of Elements with phosphorus- or nitrogen-containing ligands to give a mixture of the adducts of the formulae II

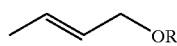

and III

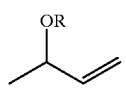

b) the adduct III is isomerized to the adduct II, c) the adduct II is converted into the acetal of the formula IV

in the presence of an amount of an alcohol ROH I sufficient to form the acetal IV and of a homogeneous or heterogeneous transition metal catalyst which differs from dicobaltoctacarbonyl or hydridocobalttetracarbonyl, in the liquid phase, under essentially anhydrous conditions, and d) n-butyraldehyde and/or n-butanol are then produced from this acetal IV by reacting it, in the liquid phase, with hydrogen and water or water in the presence of a homogeneous or heterogeneous transition metal catalyst which differs from dicobaltoctacarbonyl or hydridocobalttetracarbonyl, and the alcohol ROH I is liberated and the liberated alcohol ROH I is recycled to the reaction in reaction steps a) and/or c).

The novel process thus consists of 4 reaction steps a) to d). The reaction steps a) and b) can be carried out either individually, in succession, in at least two process stages or virtually simultaneously in a single process stage, the isomerization of the adduct III to the adduct II in reaction step b) after recycling of the adduct III to the process stage involving the addition reaction of the alcohol ROH I with 1,3-butadiene taking place simultaneously with the addition reaction in reaction step a). On the other hand, the reaction steps c) and d) are advantageously carried out in succession, in two process stages. As a result, it is possible in a simple manner to adapt the process conditions for the novel process to the local conditions of the location where a plant for carrying out the process is installed, for example by integrating plant parts already present on site into the plant for the novel process. Furthermore, the novel process may be designed so that no expensive noble metal catalysts need be used.

The term process stage is used in this application for a plant unit in which an individual reaction step a) to d) takes place over the catalyst or catalysts used in this plant unit, or in which a plurality, in particular 2, of these reaction steps take place in succession over the catalyst or catalysts used in this plant unit. The hydrolysis or the combined hydrolysis/hydrogenation of the acetal IV according to reaction step d) is considered as a single reaction step, unless stated otherwise in this application.

If the catalyst used in a plant unit or each of the catalysts used in a plant unit is or are capable of catalyzing, under the reaction conditions used there, for example the isomerization of the adduct III to the adduct II according to the reaction step b) and the addition reaction of the alcohol ROH I with 1,3-butadiene according to reaction step a), so that no strict spatial separation of the occurrence of these reaction steps can be detected in the plant unit, this application states that the reaction steps a) and b) are carried out in a single process stage. A plant unit may comprise either a single reactor or a plurality of reactors connected in series, which are filled with the same or, if required, different catalysts and are operated in the same mode of operation and under the same or different temperature and pressure conditions. Mode of operation is understood in each case as meaning operation in the liquid phase with the use of a homogeneous catalyst or operation in the liquid phase with the use of a heterogeneous catalyst. Consequently, for example, this application does not refer to a reaction in a single process stage when catalysts capable by themselves of catalyzing a certain reaction step are used in the individual, successive reactors or when different modes of operation are used in these reactors.

The reaction of the butenyl ether II to give n-butyraldehyde and/or n-butanol can also be effected starting from butenyl ethers II which have been prepared in a manner other than by the integrated process described above, for example by reacting allyl halides and an alcohol ROH I in the presence of a base. Accordingly, we have also found a process for the preparation of n-butyraldehyde and/or n-butanol, wherein an ether of the formula II

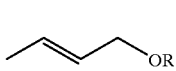

II where R is a $C_2$–$C_{20}$-alkyl or alkenyl group which is unsubstituted or substituted by 1 or 2 $C_1$–$C_{10}$-alkoxy or hydroxyl groups, or $C_6$–$C_{10}$-aryl, $C_7$–$C_{11}$-aralkyl or methyl, is converted into the acetal of the formula IV

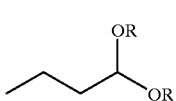

IV in the presence of an amount of an alcohol ROH I, where R has the abovementioned meanings, sufficient to form the acetal IV and in the presence of a homogeneous or heterogeneous transition metal catalyst which differs from dicobaltoctacarbonyl or hydridocobalttetracarbonyl, in the liquid phase under essentially anhydrous conditions, and n-butyraldehyde and/or n-butanol are subsequently produced from this acetal IV by reacting it in the liquid phase with hydrogen and water or water in the presence of a homogeous or heterogeneous transition metal catalyst which differs from dicobaltoctacarbonyl or hydridocobalttetracarbonyl, and the alcohol ROH I is liberated.

The novel process is described in more detail below:

In stage a), 1,3-butadiene or a butadiene-containing hydrocarbon mixture is reacted with the alcohol ROH I according to equation (1)

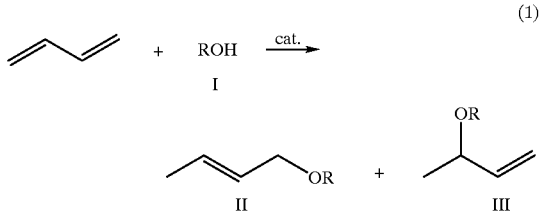

(1)

in the presence of a catalyst to give the 1,4-adduct of the formula II and the 1,2-adduct of the formula III. In the resulting 1,4-adduct II, the double bond may be present either in the cis or in the trans form, but this is not important for the further course of the process. The adducts II and III are formed in general in a molar ratio of from 1:1 to 1:3, depending on the reaction conditions and catalyst used.

The type of alcohol ROH I used in the reaction is as a rule not critical for the process. Both primary and secondary alcohols may be used, primary alcohols are however preferably employed. Aliphatic, cycloaliphatic, aromatic and araliphatic alcohols may be used, aliphatic and araliphatic alcohols being preferably employed. In general, alcohols ROH I used in the novel process are those in which R is $C_1$–$C_{20}$-alkyl, $C_3$–$C_{10}$-alkenyl, eg. allyl or but-2-enyl, $C_5$–$C_{20}$-alkadienyl, advantageously without cumulative double bonds, eg. octa-2,7-dien-1-yl-, preferably $C_1$–$C_4$-alkyl, in particular n-butyl, $C_6$–$C_{10}$-aryl, preferably phenyl, or $C_7$–$C_{11}$-aralkyl, preferably benzyl. The radicals R may be unsubstituted or substituted by $C_1$–$C_{10}$-alkoxy and/or hydroxyl. Thus, diols or triols or alkoxy alcohols may also be used as alcohols ROH I. Since these substituents generally have no critical influence on the reaction, alcohols ROH I having unsubstituted radicals R are preferably used. It is of course also possible to use alcohols having a larger number of carbon atoms; since such higher alcohols are as a rule more expensive than lower alcohols, lower alcohols are preferably used for economic reasons.

A large number of catalysts may be used as catalysts in stage a), for example Brönsted acids or phosphine complexes of transition metals of Groups IA, VIIA or VIIIA of the Periodic Table of Elements, in particular phosphine complexes of palladium and of nickel.

The Brönsted acids used may be, for example, conventional, nonoxidizing Brönsted acids, such as hydrohalic acids, eg. hydrochloric acid, sulfuric acid, phosphoric acid, perchloric acid, hydrofluoric acid, tetrafluoroboric acid, methanesulfonic acid or toluenesulfonic acid, but solid Brönsted acids, in particular organic or inorganic cation exchangers, are preferably used.

Organic cation exchangers are understood as meaning pulverulent, gel-like or macroporous, polymeric polyelectrolytes which carry Brönsted acid functional groups, such as sulfonyl, phosphonyl or carboxyl groups, on a polymeric matrix, for example sulfonated phenol/formaldehyde resins, sulfonated styrene/divinylbenzene copolymers, sulfonated polystyrene, poly(perfluoroalkylene)-sulfonic acids or sulfonated carbons. In the novel process, these cation exchangers can be used in the form of commercial products, as available, for example, under the tradenames Amberlite®, Dowex®, Amberlyst®, Lewatit®, Wofatit®, Permutit®, Purolite®, and Nafion®. Advantageously, the cation exchangers are used in the novel process in their protonated form, ie. the $H^+$ from. Examples of suitable organic cation exchangers are the commercial products Amberlite® 200, Amberlite® IR 120, Amberlite® IR 132 E, Lewatit® SC 102, Lewatit® SC 104, Lewatit® SC 108, Lewatit® SPC 108, Lewatit® SPC 112, Lewatit® SPC 118, Purolite® CT 145, Purolite® CT 171, Purolite® CT 175 and Amberlyst® 15.

Advantageous results can furthermore be obtained in the novel process with modified organic cation exchangers, for example those which additionally contain Lewis acids, such as copper(II) halides, in particular copper(II) chloride, copper(II) bromide or copper(II) iodide, or copper(II) salts, such as copper(II) sulfate, copper(II) nitrate or copper(II) acetate. Such Lewis acid-containing cation exchangers can be prepared, for example, by the process of GB-A 943 160. The Lewis acid-containing ion exchangers are preferably used in a form in which only some of the hydrogen ions of the Brönsted acid groups of the ion exchanger are exchanged for the Lewis acid cation while the remaining Brönsted acid groups continue to act as Brönsted acids. In general, the organic ion exchangers are doped with an amount of Lewis acid such that from 5 to 90, preferably from 10 to 40, in particular from 15 to 30, mol-% of the hydrogen ions of the Brönsted acid groups present on the ion exchanger are exchanged for the relevant Lewis acid.

Instead of organic, acidic cation exchangers, inorganic solids having Brönsted acid activity may also be used in the novel process, for example zeolites, such as β-zeolites or Y-zeolites in the H⁺ form, bleaching earths, such as bentonites, montmorillonites or attapulgites, phosphate-based non-zeolite molecular sieves, as disclosed in, for example, U.S. Pat. No. 4,440,871, U.S. Pat. No. 4,310,440, U.S. Pat. No. 4,567,029, U.S. Pat. No. 4,554,143, U.S. Pat. No. 4,500,651, EP-A 158 976, EP-A 158 349 and EP-A 159 624, and acidic or acid-impregnated metal oxides, the preparation of which is described, for example, in U.S. Pat. No. 4,873,017. Preferred inorganic solids having Brönsted acid activity are β-zeolites or Y-zeolites in the H⁺ form, in particular β-zeolites in the H⁺ form. β-Zeolites are obtainable, for example, by the process of U.S. Pat. No. 4,891,458.

Organic ion exchangers are particularly preferably used in the novel process for the addition reaction of alcohols ROH I with 1,3-butadiene or butadiene-containing hydrocarbon mixtures in reaction step a).

If liquid or dissolved Brönsted acid catalysts are used in reaction step a) of the novel process, in particular sulfuric acid, phosphoric acid, toluenesulfonic acid, methanesulfonic acid or tetrafluoroboric acid, the procedure generally adopted is one in which 1,3-butadiene or the butadiene-containing hydrocarbon mixture in gaseous or, preferably, in liquid form is passed into the initially taken acid/alcohol mixture and the resulting adducts of the formulae II and III are removed from the reaction zone by distillation or by stripping. Conventional reactors, such as bubble columns, loop reactors, etc., may be used for this purpose. Advantageously, the alcohol/1,3-butadiene mixture can be introduced into the acid solution, for example, by means of jets. The adducts II and III can be separated off from the aqueous solution of the Brönsted acid also by means of phase separators. Instead of bubble columns or loop reactors, stirred kettle cascades may also be used, the reaction advantageously being carried out at a pressure at which the 1,3-butadiene is liquid under the chosen reaction conditions.

In the novel process, however, solid Brönsted acids in the form of the abovementioned organic or inorganic catalysts are preferably used, in particular organic ion exchangers. These are preferably arranged in a fixed bed, through which the liquid reaction mixture flows in the liquid-phase or, preferably, trickle-bed procedure. The fixed catalyst bed can be installed, for example, in tube reactors or, preferably, in reactor cascades. It is also possible to pass the reactants in gaseous form through the catalyst bed, but the liquid phase is preferably employed. Of course, the addition reaction of the alcohol ROH I with 1,3-butadiene or butadiene-containing hydrocarbon mixtures according to reaction step a) can be carried out either continuously or batchwise.

In the novel process, the molar alcohol/1,3-butadiene ratio can be chosen from a wide range. In general, a molar alcohol ROH/1,3-butadiene ratio of from 0.5:1 to 8.0:1, preferably from 1:1 to 5.0:1, and particularly preferably from 1.5:1 to 3.0:1, is used. The reaction of the alcohol ROH I with 1,3-butadiene is effected in general at from 20 to 150° C., preferably from 50 to 120° C., in particular from 60 to 110° C., and at in general from 1 to 100, preferably from 3 to 50, in particular from 5 to 30, bar when the process is carried out in the liquid phase. The pressure is advantageously chosen so that the 1,3-butadiene or the butadiene-containing hydrocarbon mixtures are liquid at the reaction temperature used. The use of a higher pressure is possible. The reaction temperature used is advantageously optimized in a preliminary experiment with respect to the respective Brönsted acid catalyst used.

In general, the alcohol ROH/1,3-butadiene mixture is passed at a space velocity of from 0.01 to 0.5, preferably from 0.05 to 0.4, particularly preferably from 0.10 to 0.25, g/cm³·h through the fixed catalyst bed. The addition of a solvent to the reaction mixture is possible but is generally not necessary since the alcohol used as well as the adducts II and III may also act as solvents. The residence time of the alcohol ROH/1,3-butadiene mixture in the reactor is in general from 1 to 6 hours and is as a rule dependent on the reaction temperature used.

If the addition reaction of the alcohol ROH I with 1,3-butadiene or the butadiene-containing hydrocarbon mixtures is carried out in the gas phase, in general temperatures of less than 120° C. and a pressure of in general less than 20 bar are used. If desired, the reaction gas can be mixed with a gas which is inert under the reaction conditions, eg. nitrogen, but in general the reaction gas is used undiluted.

In a further embodiment of the novel process, the addition reaction of the alcohol ROH I can be effected by means of a transition metal catalyst which is homogeneously dissolved in the reaction medium or is heterogeneous and which contains an element from Group IA, VIIA or VIIIA of the Periodic Table of Elements, such as copper, nickel, rhodium, palladium, platinum or iridium, preferably palladium or nickel.

These transition metal catalysts, in particular the palladium and nickel catalysts, are advantageously used in the form of their complexes with, for example, phosphine, 2,2'-bipyridine or 1,10-phenanthroline ligands, which complexes are homogeneously soluble in the reaction medium. For this purpose, a large number of different phosphine, 2,2'-bipyridine or 1,10-phenanthroline ligands can be used for complexing the Group IA, VIIA or VIIIA metals, in particular palladium and nickel, in the novel process. Both monodentate and polydentate, in particular bidentate, phosphine ligands may be used. Suitable phosphine ligands are, for example, trialkylphosphines, triarylphosphines, alkyldiarylphosphines, aryldialkylphosphines, aryldiphosphines, alkyldiphosphines and arylalkyldiphosphines. The alkyl-carrying phosphine ligands may contain identical or different $C_1$–$C_{20}$-, preferably $C_1$–$C_6$-alkyl or -cycloalkyl groups. The aryl-carrying phosphine ligands may contain identical or different $C_6$–$C_{12}$-aryl groups, in particular phenyl or naphthyl, but also diphenyl groups. Phosphine ligands which carry heterocycloaliphatic groups, such as pyrrolidine, imidazolidine, piperidine, morpholine, oxazolidine, piperazine or triazolidine groups, or heteroaromatic groups, such as pyrrole, imidazole, oxazole, indole, pyridine, quinoline, pyrimidine, pyrazole, pyrazine, pyridazine or quinoxaline groups, together with other alkyl or aryl groups may furthermore be used for complexing the Group IA, VIIA or VIIIA elements. The alkyl or aryl groups of the ligands may be unsubstituted or may carry substituents which are inert under the reaction conditions, such as $C_1$–$C_4$-alkoxy, di-$C_1$–$C_4$-alkylamino, $C_1$–$C_6$-alkyl, nitro, cyano or sulfonate groups. Examples of sulfonated phosphine ligands suitable in the novel process are in particular triphenylphosphine trisulfonate (TPPTS) and triphenylphosphine monosulfonate (TPPMS) (Angew. Chem. 105, (1993) 1588).

In principle, there is no restriction to the applicability of such ligands for complexing the Group IA, VIIA or VIIIA elements, in particular palladium and nickel, in the novel process. For cost reasons, however, ligands which can be prepared in a simple manner are preferably used.

A list of such ligands which serves merely by way of example is given below: trimethylphosphine, triethylphosphine, tripropylphosphine, triisopropylphosphine, tributylphosphine, trioctylphosphine, tridecylphosphine, tricyclopentylphosphine, tricyclohexylphosphine, triphenylphosphine, tritolylphosphine, cyclohexyldiphenylphosphine, tetraphenyldiphosphinomethane, 1,2-bis(diphenylphosphino)ethane, tetramethyldiphosphinomethane, tetraethyldiphosphinomethane, 1,3-bis(diphenylphosphino)propane, 1,4-bis(diphenylphosphino)butane, tetra-t-butyldiphosphinomethane, 1,2-bis(dimethylphosphino)ethane, 1,2-bis(diethylphosphino)ethane, 1,2-bis(dipropylphosphino)ethane, 1,2-bis(diisopropylphosphino)ethane, 1,2-bis(dibutylphosphino)ethane, 1,2-bis(di-t-butylphosphino)ethane, 1,1-bis(dicyclohexylphosphino)methane, 1,2-bis(dicyclohexylphosphino)ethane, 1,4-bis(dicyclohexylphosphino)butane, and the bisphosphine ligands described in EP-A 279 018, EP-A 311 619, WO 90/06810 and EP-A 71 281. Preferred phosphine ligands in addition to triphenylphosphine (abbreviated to PPh$_3$) are bidentate phosphine ligands bridged via $C_1$–$C_4$-alkylene groups and of the general formula

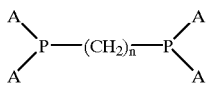

where n is an integer from 1 to 4 and the radicals A are identical or different $C_1$–$C_{10}$-alkyl or $C_5$- or $C_6$-cycloalkyl groups, of which some typical members were stated above by way of example.

Apart from being prepared by the processes described in the abovementioned patent applications, the alkyl- and arylphosphine ligands can be prepared by conventional methods, for example by the processes stated in Houben-Weyl, Methoden der Organischen Chemie, Volume XII/1, 4th edition, pages 17–65 and pages 182–186, Thieme, Stuttgart, 1963 and Volume E 1, 4th edition, pages 106–199, Thieme, Stuttgart, 1982.

In addition to phosphine ligands, 2,2'-bipyridine or 1,10-phenanthroline ligands of the alkyl- or aryl-substituted or fused 2,2'-bipyridine or 1,10-phenanthroline derivatives, which contain the —N=C—C=N— group responsible for the complex-forming property of the 2,2'-bipyridine or 1,10-phenanthroline ligands, for example 2,2'-biquinoline, 4,7-diphenyl-1,10-phenanthroline, 2,9-dimethyl-4,7-diphenyl-1,10-phenanthroline, 4,5-diazafluorene, dipyrido[3,2-a:2',3'-c]phenazine, 2,2',6',2"-terpyridine and the like, can also be used in the novel process. Some of these ligands are commercially available, eg. 2,2'-bipyridine or 1,10-phenanthroline, and others can be prepared by the methods stated in Synthesis 1, (1976) or Aust. J. Chem. 23, (1970) 1023.

The complexes of the elements of Group IA, VIIA or VIIIA, in particular of palladium and nickel, which can be used in the novel process for reaction step a) can be produced in situ in the reaction mixture or formed beforehand and then added to the reaction mixture. For the in situ production of these complexes, in general compounds of Group IA, VIIA or VIIIA elements, for example their halides, preferably their chlorides, bromides or iodides, the nitrates, cyanides or sulfates or, particularly preferably complex compounds of these metals, such as acetylacetonates, carboxylates, carbonyl complexes or olefin complexes, such as ethene or butadiene complexes, are fed to the reaction mixture together with the relevant ligands, whereupon the complexes which can be used according to the invention in reaction step a) form in the reaction mixture. In general, the relevant ligand with respect to the Group IA, VIIA or VIIIA element is added here in a molar ratio of from 1 to 200, preferably from 1 to 50, in particular from 1 to 10.

In general, a molar 1,3-butadiene/Group IA, VIIA or VIIIA element ratio of from 100:1 to 100000:1, preferably from 200:1 to 5000:1, particularly preferably from 400:1 to 2500:1, is established in the addition reaction of the alcohol ROH I with 1,3-butadiene or with 1,3-butadiene in butadiene-containing hydrocarbon mixtures in step a) of the novel process when the stated group IA, VIIA or VIIIA complex catalysts, particularly palladium or nickel complex catalysts, are used, this molar ratio being based on the steady-state 1,3-butadiene concentration in the liquid reaction mixture in the case of the continuous process.

The molar alcohol ROH I/1,3-butadiene ratio in this process embodiment can be chosen within wide limits and is as a rule not critical. For example, the alcohol to be subjected to the addition reaction with 1,3-butadiene may act not only as a reagent but also as a solvent for the complex catalyst. In general, a molar alcohol/1,3-butadiene ratio of from 0.5:1 to 10:1, preferably from 1:1 to 5:1, particularly preferably from 1:1 to 3:1, is therefore used in reaction step a) in the novel process, these data being based on the steady-state 1,3-butadiene concentration in the liquid reaction mixture in the case of the continuous embodiment of the process.

The addition reaction of the alcohol ROH I with 1,3-butadiene according to reaction step a) of the novel process with the aid of the stated complex catalysts is preferably carried out in the liquid phase. In general, the catalyst, dissolved in the liquid reaction medium, is initially taken and 1,3-butadiene or the butadiene-containing hydrocarbon mixture is passed in liquid or gaseous form, together with the alcohol I, into the reaction mixture. The alcohol to be subjected to the addition reaction with 1,3-butadiene or a solvent which is inert under the reaction conditions, preferably a high-boiling solvent, may serve as the reaction medium. The examples of suitable solvents are condensates which form in the course of the reaction, such as alkoxyoctadienes, alkoxydodecatrienes, and ethers, such as dibutyl ether or dioctyl ether, diethylene glycol dibutyl ether, low molecular weight, liquid polyethylene glycol ethers and sulfones, such as sulfolane, or hydrocarbons, such as Mihagol. Mihagol is a commercially available $C_{10}$–$C_{14}$-hydrocarbon mixture. It is of course also possible to use mixtures of different solvents as the reaction medium.

In the batchwise embodiment of the process, the reaction is generally carried out in a stirred autoclave. The resulting adducts of the formulae II and III are then advantageously separated from the reaction mixture by distillation, the homogeneous catalyst containing the Group IA, VIIA or VIIIA element, in particular palladium or nickel, remaining behind in the bottom product of the distillation, dissolved in the high-boiling solvent. The catalyst solution thus remaining in the bottom product of the distillation can, if desired, be reused for further reactions.

In the continuous embodiment of the process, the 1,3-butadiene or the butadiene-containing hydrocarbon mixture is fed, preferably in liquid form under pressure, into the reaction mixture containing the alcohol ROH I and the homogeneously dissolved transition metal complex catalyst and, if required, a high-boiling solvent. The reaction is advantageously carried out in a tube reactor, loop reactor or, preferably, a reactor cascade. Unconverted 1,3-butadiene is advantageously circulated. The alcohol ROH I is advantageously metered continuously to the reaction mixture at the rate at which it is consumed in the reaction.

In a further continuous embodiment of the novel process, the 1,3-butadiene or the butadiene-containing hydrocarbon mixture can be passed in gaseous form through the liquid reaction medium containing the catalyst, unconverted 1,3-butadiene and the readily volatile hydrocarbons being used for stripping the relatively readily volatile adducts of the formulae II and III formed in the reaction with the alcohol from the reaction mixture. The alcohol ROH I can be metered continuously to the reaction mixture at the rate at which it is consumed in the reaction.

The addition reaction of the alcohol ROH I with 1,3-butadiene in the presence of the stated complexes of the Group IA, VIIA or VIIIA elements, in particular of palladium or nickel, is generally carried out at from 20 to 180° C., preferably from 40 to 150° C., particularly preferably from 60 to 120° C., and at preferably from 1 to 20 bar, particularly preferably under the autogenous pressure of the reaction system.

Advantageously, heterogeneous complex catalysts, preferably those in which the Group IA, VIIA or VIIIA element, in particular the palladium or nickel, is fixed to polymeric matrices, may be used in reaction step a) in the novel process for the addition reaction of the alcohol ROH I with 1,3-butadiene. Such polymeric matrices may be resins, such as styrene/divinylbenzene resins or phenol/formaldehyde resins, to which the relevant ligands, ie. phosphines, 1,10-phenanthrolines or 2,2'-bipyridines, are generally covalently bonded, which ligands in turn form complexes with the Group IA, VIIA or VIIIA elements, in particular palladium or nickel, and thus more or less immobilize them. Inorganic carrier materials, after hydrophobic and chemical modification of their surfaces by means of organic reagents, can also serve as heterogeneous matrices for immobilizing the Group IA, VIIA or VIIIA complexes, in particular the palladium or nickel complexes. Such heterogeneous, polymer-bound Group IA, VIIA or VIIIA complexes, in particular palladium and nickel complexes, are obtained, for example, by the process of Zhuangyu et al. (Reactive Polymers 9, (1988), 249) or according to Wang et al. (J. Org. Chem. 59, (1994) 5358). Immobilized phosphine complexes of the Group IA, VIIA and VIIIA elements are obtainable, for example, by the processes of Hartley, Adv. Organomet. Chem. 15, (1977), 189, F. R. Hartley "Supported Metal Complexes", Riedel, Dordrecht 1985, K. Smith, "Solid Supports and Catalysis in Organic Synthesis", Ellis Horwood, Prentice Hall, N.Y. 1992, C. H. Pittman "Polymer supported Reactions in Organic Synthesis", page 249, Wiley, Chichester 1980 and C. H. Pittmann J. Am. Chem. Soc. 98, (1976), 5407, and Ann. N.Y. Acad. Sci. 245, (1977), 15. The advantage of using such heterogeneous catalysts is in particular the easier and gentler separability of the catalyst from the reaction products. Said catalyst may be arranged in a fixed bed through which the reaction mixture flows or may be suspended in the reaction mixture and separated off mechanically after the end of the reaction.

Instead of pure 1,3-butadiene, 1,3-butadiene-containing hydrocarbon mixtures may also be used as raw material in the novel process. Such hydrocarbon mixtures are obtained, for example, as a $C_4$ cut in steam crackers. Before being used in the novel process, these hydrocarbon mixtures are advantageously freed from any acetylenic or allenic hydrocarbons present therein by partial hydrogenation thereof (Weissermel, Arpe: Industrielle Organische Chemie; 3rd edition, VCH Verlagsgesellschaft, Weinheim 1988) and, if desired, from isobutene. The 1,3-butadiene-containing hydrocarbon mixture may then be introduced, similarly to pure 1,3-butadiene, into reaction step a) of the novel process.

Advantageously, the saturated or monoolefinic hydrocarbons which are contained in these reaction mixtures and have not reacted in reaction step a) are removed from the reacted mixture of reaction step a), for example by means of a gas-liquid separator. The adducts of the formulae II and III obtained in the reaction of these hydrocarbon mixtures in reaction step a) of the novel process can, as described below, be further processed to n-butyraldehyde and/or n-butanol in the same manner as the adducts II and III produced with pure 1,3-butadiene in reaction step a).

The reacted mixture from reaction step a) of the novel process contains in general, in addition to unconverted 1,3-butadiene or saturated or olefinic hydrocarbons, the adducts of the formulae II and III and, particularly with the use of Brönsted acids as catalysts in reaction step a), may contain a plurality of isomers of the relevant alkoxyoctadiene, which are referred to below by the collective term alkoxyoctadiene. In the addition reaction of the alcohol ROH I with 1,3-butadiene, the alkoxyoctadiene is formed in a secondary reaction in which 1,3-butadiene is first dimerized to octatriene, with which the alcohol ROH I subsequently undergoes an addition reaction with the formation of an alkoxyoctadiene. In addition to these components, the reacted mixture from reaction step a) may also contain small amounts of other byproducts, for example dibutyl ether, octatriene, vinylcyclohexene, alkoxydodecatrienes, formed by trimerization of the 1,3-butadiene to dodecatetraene and subsequent addition of the alcohol ROH I, and dodecatetraene, dialkoxyoctene and dialkoxybutane. The formation of these byproducts can be influenced and, if desired, minimized through the manner in which the reaction is effected in reaction step a), for example by the choice of the 1,3-butadiene/alcohol ROH I ratio in the reaction mixture, and the choice of the reaction temperature and of the pressure.

The adduct required for the preparation of n-butyraldehyde and/or n-butanol in the novel process is the 1-alkoxybut-2-ene of the formula II, which, for the preparation of the desired compounds of the novel process, can be separated from its isomer 3-alkoxybut-1-ene of the formula III which is contained in roughly the same amount in the reacted mixture. Since the adducts II and III are formed in roughly the same amounts in the addition reaction of the alcohol ROH I with 1,3-butadiene, the novel process would not be economical on a large industrial scale if it were not possible to convert the 3-alkoxybut-1-ene III in an economical manner into the desired 1-alkoxybut-2-ene II. It was found that the conversion of the adduct III into the desired adduct II can be effected in a simple and economical manner.

For this purpose, the adduct III is first separated from the isomeric adduct II contained in the reacted mixture of reaction step a). This can be advantageously effected by passing the reacted mixture from reaction step a), after prior removal of unconverted 1,3-butadiene, for example in a gas-liquid separator, into a distillation apparatus and effecting separation therein by fractional distillation.

In this fractional distillation, the byproducts contained in the reacted mixture of reaction step a), 1,3-butadiene dimers and trimers and adducts thereof with the alcohol ROH I and any polyalkoxylated byproducts can also be separated from the adduct II. Since these byproducts are generally not troublesome in the further course of the novel process, they need not be separated off. In another distillation procedure, only a part of the byproducts, in particular the olefinic 1,3-butadiene dimers and trimers and polyalkoxylated byproducts, can be separated off in addition to the adduct III, whereas other byproducts, in particular the alkoxyoctadiene and, if desired, the alkoxydodecatriene, may be further processed together with the adduct II in the subsequent reaction steps, octanols and dodecanols, respectively, which are desirable plasticizer alcohols, being formed as end products from these byproducts of reaction step a).

Separation of the more readily volatile adduct III from the adduct II by distillation is carried out in a simple manner, for example in a conventional distillation column. The adduct III separated from the desired adduct can, as in the case of the unconverted 1,3-butadiene, then be recycled to the process stage of reaction step a) of the novel process. Said recycling of the adduct III results in isomerization of the adduct III to give the adduct II in this process stage and finally leads to suppression of the reformation of the undesired adduct III, so that, when this circulation procedure is used, virtually only the desired adduct II, but not its undesired isomer III, is formed in the overall balance of this circulation process.

Instead of being effected by recycling of the adduct III to the process stage of reaction step a) of the novel process, the isomerization of said adduct can also be carried out in a separate isomerization step, by passing the adduct III separated from the adduct II, for example, through an isomerization reactor loaded with one of the catalysts which may be used in reaction step a), separating this reactor discharge, which consists of the isomerization mixture formed therein and comprising adduct III and adduct II, into adduct II and adduct III, for example by distillation, further processing the newly formed adduct II in the further course of the novel process to give n-butyraldehyde and/or n-butanol and recycling the adduct III to the isomerization reactor.

The isomerization of the adduct III to give the adduct II in the isomerization reactor can be carried out in the presence or absence of a solvent. The addition of a solvent may be advantageous in particular when one of the abovementioned complexes of an element of Group IA, VIIA or VIIIA of the Periodic Table of Elements is used as the isomerization catalyst. If the isomerization is carried out in the presence of a solvent, in general high-boiling solvents, such as ethers, for example di- or triethylene glycol dimethyl ether or di- or triethylene glycol dibutyl ether, sulfoxides, eg. dimethyl sulfoxide, or sulfones, such as sulfolane, high-boiling aromatic or aliphatic hydrocarbons or halogenated aliphatic or aromatic solvents, eg. dichlorobenzene, are used. The use of low-boiling solvents is also possible but as a rule requires a more complicated procedure in the distillative separation of the discharge from the isomerization reactor into the adducts II and III.

In the further course of the novel process for the preparation of n-butyraldehyde and/or n-butanol, the adduct II is catalytically converted in reaction step c) with an alcohol ROH I into the acetal of the formula IV, which is then catalytically hydrolyzed in reaction step d) in the presence of water to give n-butyraldehyde and/or catalytically converted in the presence of water and hydrogen to give n-butanol. In the novel process, the reaction steps c) and d) can be carried out either successively in two process stages or successively in a single reactor.

As stated, the reaction steps c), the isomerization and acetalation of the adduct II to give the acetal IV, and d), its reaction with water or hydrogen and water to give n-butyraldehyde and/or n-butanol, are preferably carried out successively. These reaction steps comprise the following chemical reactions according to equations (2):

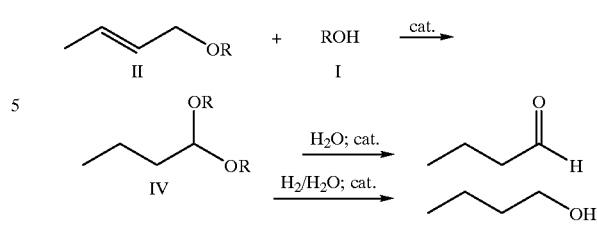

The reaction of the allyl ether II with an alcohol ROH I to give the acetal IV may take place via the enol ether intermediate V

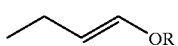

which might form as a result of isomerization of the allyl ether II. Although this course of the reaction was not investigated in more detail and is thus not proven, the fact that the enol ether V can be isolated as a byproduct under certain reaction conditions indicates such a reaction mechanism. The formation of such enol ether byproducts is not critical for the cost-efficiency of the novel process since the enol ether can be separated off from the desired end product, eg. from the butyraldehyde, after isolation and can be recycled to the reaction in reaction steps c) and/or d), where it is converted into the desired end product. Alternatively, the enol ether byproduct can also be removed from the process circulation, after, for example, separation from the end product by distillation as the novel process [sic], and can be put to other uses, for example for the preparation of the corresponding saturated ethers by selective hydrogenation of the double bond. Such ethers are used, for example, as solvents.

For the reaction according to reaction step c), it is possible in principle to use the same alcohols ROH I which can be used for carrying out reaction step a) and which have been described in the explanation of reaction step a) in this application. The alcohol ROH I used for carrying out reaction step c) may be the same alcohol as that used in the preceding reaction step a) but may also differ therefrom. Mixtures of a plurality of alcohols ROH I may of course also be fed to reaction step c). However, the alcohol ROH I used in reaction step c) may be the same as that used in reaction step a), and in this case the alcohol ROH I is also most preferably n-butanol.

It is self evident to a person skilled in the art that cyclic acetals IV, too, can be formed when an alcohol I having at least two hydroxyl groups is used. The respective final reaction step, ie. the hydrolysis of the acetal IV to n-butyraldehyde on the one hand or the combined hydrolysis/hydrogenation of the acetal IV to n-butanol on the other hand, can be controlled by the choice of the reaction conditions, in particular by the choice of the catalyst and the choice of the amount of reactants, water and hydrogen, made available in the reaction, so that alternatively the end product n-butyraldehyde or n-butanol is selectively formed or that mixtures of these two desired products form as the end product of the novel process.

It was found, surprisingly, that the catalysts to be used according to the invention, which catalyze the reaction of the adduct II to the acetal IV, are also generally suitable as catalysts for the hydrolysis of the acetal IV to n-butyraldehyde or for the combined hydrolysis/hydrogenation of the acetal IV to n-butanol. Accordingly, in a particularly preferred embodiment of the novel process, the same catalysts may be used in both reaction step c) and reaction step d), regardless of whether n-butyraldehyde and/or n-butanol are to be produced as the end product.

Both the acetalation of the adduct II to the acetal IV and the hydrolysis of the acetal IV to n-butyraldehyde or the combined hydrolysis/hydrogenation of the acetal IV to n-butanol are carried out in the liquid phase. In carrying out these reaction steps, both homogeneous and heterogeneous catalysts are used.

In a particularly preferred embodiment of the novel process, the acetalation of the adduct II to the acetal IV and its hydrolysis or combined hydrolysis/hydrogenation to n-butyraldehyde and/or n-butanol are carried out in succession using a homogeneous catalyst.

A large number of transition metal compounds may be used as homogeneous catalysts for the acetalation of the adduct II to the acetal IV and its hydrolysis or combined hydrolysis/hydrogenation to n-butyraldehyde and/or n-butanol, in particular transition metal compounds which contain elements from subgroup VI and VIII of the Periodic Table of Elements, preferably molybdenum, iron, cobalt, nickel and in particular the platinum metals ruthenium, rhodium, palladium, platinum, osmium and/or iridium, particularly preferably ruthenium, rhodium, iridium or osmium. However, dicobaltoctacarbonyl($Co_2(CO)_8$) and hydridocobalttetracarbonyl ($HCo(CO)_4$) are excluded therefrom.

Examples of suitable catalysts are the salts of these transition metals, preferably those of the platinum metals, in particular the halides, nitrates, sulfates, phosphates, carboxylates, for example their $C_1$–$C_{20}$-carboxylates, such as formates, acetates, trichloroacetates, propionates, 2-ethylhexanoates, 2-propylheptanoates and decanoates, and sulfonates, for example methanesulfonates, benzenesulfonates, naphthalenesulfonates, toluenesulfonates, trifluoromethylbenzenesulfonates or trifluoromethanesulfonates, cyanides, tetrafluoroborates, perchlorates or hexafluorophosphates, which are soluble in the reaction medium, soluble inorganic complex compounds of these elements, in particular their hydrated, amine, halo, phosphine, phosphite, cyano or amino complexes and the complexes of these transition metals with chelate formers, such as acetylacetone, dioximes, for example diacetyldioxime, furildioxime or benzildioxime, ethylenediaminetetraacetic acid, nitrilotriacetic acid, nitrilotriethanol, ureas or thioureas, bisphosphines, bisphosphites, bipyridines, terpyridines, phenanthrolins, 8-hydroxyquinoline, crown ethers or polyalkylene glycoles, and organometallic compounds of these transition metal elements, for example carbonyl complexes, such as $HRuCl(CO)(PPh_3)_3$, $HRuCl(CO)(hexyldiphenylphosphine)_3$, $RuH_2(CO)(PPh_3)_3$, $RuH(CO)(CH_3CO_2)(PPh_3)_2$, $RuH_2(PPh_3)_4$ or $IrCl(CO)(PPh_3)_3$.

Preferred salt-like homogeneous catalysts are the halides, in particular the chlorides, nitrates, sulfates, sulfonates, carboxylates and cyanides of rhodium, of ruthenium, of palladium, of platinum and of iridium.

Inorganic complex compounds which are preferably used in the novel process for carrying out the reaction steps c) and d) are, for example, ruthenium trichloride, rhodium trichloride or iridium hexaaquaditosylate.

Preferred homogeneous catalysts for carrying out the reaction steps c) and d) are furthermore complexes of the stated transition metal elements, in particular of cobalt, of nickel, of rhodium, of ruthenium, of palladium, of platinum, of osmium and of iridium, with monodentate or polydentate, in particular bidentate, phosphine or phosphite ligands and/or with nitrogen-containing ligands, for whose property as a complexing agent the (—N═C—C═N—) structural unit is responsible, for example 2,2'-bipyridine or 1,10-phenanthroline, and the ligands derived from these parent substances by substitution or fusion. Among the abovementioned complexes, the phosphine or phosphite complexes in turn, in particular the phosphine complexes of the platinum metals ruthenium, rhodium, iridium and osmium, are particularly preferred.

Suitable phosphine ligands are, for example, the phosphine ligands which are suitable for carrying out reaction step a) of the novel process and are mentioned in the description of this reaction step in this application and which are hereby referred to. Triphenylphosphine and the stated alkylene-bridged bisphosphine ligands (loc. cit.) are particularly preferred. Suitable 2,2'-bipyridine or 1,10-phenanthroline ligands are, for example, the 2,2'-bipyridine or 1,10-phenanthroline ligands which are suitable for carrying out reaction step a) of the novel process and are mentioned in the description of this reaction step, and their stated derivatives and structural analogs (loc. cit.), which are hereby referred to.

Suitable phosphite ligands are, for example, trialkylphosphites, alkyldiarylphosphites, triarylphosphites, alkyl bisphosphites, aryl bisphosphites and alkyl aryl bisphosphites. The alkyl-carrying phosphite ligands may contain identical or different $C_1$–$C_{10}$-, preferably $C_1$–$C_6$-alkyl or cycloalkyl groups. The aryl-carrying phosphite ligands may contain identical or different $C_6$–$C_{12}$-aryl groups, in particular phenyl or naphthyl, but also diphenyl or binaphthyl. Furthermore, phosphite ligands which carry heterocycloaliphatic groups, such as pyrrolidine, imidazolidine, piperidine, morpholine, oxazolidine, piperazine or triazolidine groups, or heteroaromatic groups, such as pyrrole, imidazole, oxazole, indole, pyridine, quinoline, pyrimidine, pyrazole, pyrazine, pyridazine or quinoxazoline groups, together with other alkyl or aryl groups may be used for complexing the transition metals. The alkyl or aryl groups of the phosphite ligands may be unsubstituted or may carry substituents which are inert under the reaction conditions, such as $C_1$–$C_4$-alkoxy, di-$C_1$–$C_4$-alkylamino, $C_1$–$C_6$-alkyl, hydroxyl, nitro, cyano or sulfonate. The sulfonate-substituted phosphite ligands and their complexes are in general water-soluble. Suitable phosphite ligands are, for example, trimethyl phosphite, triethyl phosphite, tripropyl phosphite, triisopropyl phosphite, tributyl phosphite, tricyclopentyl phosphite, tricyclohexyl phosphite, triphenyl phosphite and the mono- and bisphosphite ligands described in EP-A 472 071, EP-A 213 639, EP-A 214 622, DE-A 2 733 796, EP-A 2261, EP-A 2821, EP-A 9115, EP-A 155 508, EP-A 353 770, U.S. Pat. No. 4,318,845, U.S. Pat. No. 4,204,997 and U.S. Pat. No. 4,362,830.

Among the abovementioned organometallic compounds of the transition metals, carbonyl complexes of the platinum metals which contain phosphorus-containing ligands, in particular phosphine ligands, such as $HRh(PPh_3)_3(CO)$, $IrCl(CO)(PPh_3)_3$, $[Ir(cod)PPh_3)_2]PF_6$ (cod is the abbreviation for the 1,5-cyclooctadiene ligand), $HRuCl(PPh_3)_3(CO)$, $HRu(CO)(CH_3COO)(PPh_3)_2$, $H_2Ru(CO)(PPh_3)_3$, $RuCl_2(CO)_2(PPh_3)_3$ or $RuH(CO)(C_9H_{19}COO)(PPh_3)_2$—$C_9H_{19}COO$ is the capric acid anion—are particularly preferred as homogeneous catalysts for carrying out reaction steps c) and d), Among these homogeneous catalysts in turn, the halogen-free complexes are preferred, for example those which contain, as ligands, the conjugated base of an O—H-acidic, organic compound, O—H-acidic, organic compounds being understood as meaning those compounds which are acidic in aqueous solution, such as monocarboxylic acids, monosulfonic acids or non-chelating phenols. Advantageously used ligands of this type are $C_2$–$C_{30}$-carboxylic acid anions, which preferably originate from a monocarboxylic acid such as acetate, propionate, butyrate, isobutyrate, valerate, pivalate, caproate, enanthate, caprylate, 2-ethylhexanoate, 2-propylheptanoate, caprate, laurate, myristate, palmitate, stearate, oleate, benzoate, alkylbenzoate, naphthoate and alkylnaphthoate anions or nonchelating phenolate anions or sulfonate anions.

Phenolates which can be advantageously used as ligands in such organic transition metal compounds effective as homogeneous catalysts for reaction steps c) and d) are, for example, phenolate and naphtholate anions and phenolate and naphtholate anions substituted by substituents which are inert under the reaction conditions of reaction steps c) and d), for example $C_1$–$C_{20}$-alkyl-substituted, preferably $C_1$–$C_{10}$-alkyl-substituted, phenolates or naphtholates, such as methylphenolate, nonylphenolate, 2,6-di-tert-butylphenolate or 2,6-di-tert-butyl-4-methylphenolate anions.

Sulfonate ligands which can advantageously be used for this purpose are, for example, alkanesulfonates, such as the methanesulfonate, octanesulfonate, dodecanesulfonate, octadecanesulfonate or trifluoromethanesulfonate anion or arylsulfonates, such as the toluenesulfonate anion.

The preparation of the homogeneous catalysts which contain ligands originating from from [sic] acidic organic compounds and can be used according to the invention is outlined briefly below for the abovementioned ruthenium complex compounds as typical examples of similar complex compounds of other transition metals:

The complexes containing carboxylate ligands can be prepared, for example, starting from $RuH_2(PPh_3)_3(CO)$, which is obtainable, for example, according to Uttley et al, Inorganic Syntheses, Vol. XVII, (1977), 125, by reaction with the corresponding carboxylic acids by methods similar to those derived by Robinson et al, J. Chem. Soc., Dalton Trans. (1973), 1912, Frediani et al, ibid. (1990), 165, ibid. (1990), 1705, ibid. (1990), 3663, and Frediani et al, J. Organomet Chem. C17–C19 (1993) 454. The corresponding complexes containing phenolate ligands can be obtained similarly by the reaction of $H_2Ru(CO)(PPh_3)_3$ with the relevant phenols. Complexes containing sulfonate ligands are obtainable, for example, by the process described in U.S. Pat. No. 4,892,955. The halogen-containing homogeneous catalysts can be prepared, for example, by the processes of Uttley et al, Inorganic Syntheses, Vol.XV, (1974), 45, by the reaction of $RuCl_3$ with formaldehyde.

The abovementioned catalysts can be added as such to the reaction batch or—this applies in particular to the homogeneous catalysts containing carboxylate or phenolate ligands—can be produced in situ in the reaction mixture by reacting $RuH_2(PPH_3)_3(CO)$ [sic] with the relevant carboxylic acid or the relevant phenol.

Starting from complexes which have no hydrido ligands, complexes containing hydrido ligands can also be produced in situ in the presence of elemental hydrogen $H_2$, for example under the conditions of the hydrogenation reaction according to reaction step d).

Organometallic compounds of transition metals, in particular organoruthenium compounds, which are modified in this manner with carboxylate, sulfonate or phenolate ligands and additionally contain carbonyl- and/or phosphorus-containing ligands, in particular phosphine or phosphite ligands, preferably phosphine ligands, are distinguished, as homogeneous catalysts for the catalysis of reaction steps c) and d) in the novel process, both by high activity and selectivity and by high stability and hence a long time on stream. High activity and selectivity of these homogeneous catalysts relates both to the conversion of the adduct II and to the acetal IV and to the hydrolysis or combined hydrolysis/hydrogenation of the acetal IV to give butyraldehyde or butanol. Consequently, the selectivity and the cost-efficiency of the total process are also advantageously influenced.

The advantageous properties of these homogeneous catalysts can be additionally improved by carrying out the reaction according to reaction steps c) and d) in the presence of an amount, over and above the stoichiometric amount required for the formation of the transition metal carboxylate or phenolate complex, of the relevant acidic compound so that the relevant acidic compound is present in the reaction mixture in free form in equilibrium with the organic transition metal compound serving as the homogeneous catalyst. The acidic compound used for this purpose is advantageously the same as that bonded to the transition metal in the organic transition metal compound, but the addition of other acidic organic compounds is equivalent to this measure. In general, the acidic organic compound is used in a molar ratio of 1:1, based on the organic transition metal compound acting as the homogeneous catalyst.

Although the addition of hydrogen to the reaction mixture is not essential for the preparation of the end product n-butyraldehyde, the addition of small amounts of hydrogen, if necessary together with the addition of small amounts of carbon monoxide where carbonyl-containing homogeneous catalysts are used, can lead to a prolongation of the time on stream of these homogeneous catalysts. In practice, synthesis gas can be used for this purpose. It should be noted in this context that, depending on the reaction temperature used and partial pressure used, the hydrogen and/or the carbon monoxide react with the transition metal complexes present as homogeneous catalysts in the reaction mixture and consequently a plurality of catalytically active transition metal complexes which differ essentially in the number of their hydrido and carbonyl ligands may be present together in equilibrium in the reaction mixture under these conditions.

To improve the activity, selectivity and stability of the homogeneous catalysts, in particular of the homogeneous catalysts containing phosphorus-containing ligands, the phosphine or phosphite is generally added in a 2 to 100, preferably 2 to 20, particularly preferably 2 to 10, molar amount, based on the phosphine or phosphite complex of the transition metal. If the transition metal complex serving as the homogeneous catalyst is produced in situ in the reaction mixture, a correspondingly large excess, based on the relevant transition metal, of phosphine or phosphite ligand is advantageously used.

The transition metal catalysts which are homogeneously soluble in the reaction medium are generally used in amounts of from 0.001 to 1.0, preferably from 0.01 to 1.0, mol %, based on the adduct II fed to the reactor. It is evident to a person skilled in the art that the amount of homogeneous catalyst to be added depends on the catalytic activity of the homogeneous catalyst used in each case. Depending on the type of homogeneous catalyst used, it may therefore also be advantageous to add a larger or smaller amount of catalyst to the reaction mixture. The optimum amount of the homogeneous catalyst used in each case is advantageously determined in a preliminary experiment.

Reaction steps c) and d) effected with the aid of the stated homogeneous catalysts can be carried out batchwise, for example in stirred kettles, or continuously, for example in loop reactors or stirred kettle cascades, in general from 20 to 200° C., preferably from 60 to 180° C., in particular from 80 to 160° C., and in general from 1 to 100, preferably from 10 to 60, bar. The conversion of the adduct II into the acetal IV and its conversion into n-butyraldehyde and/or n-butanol can be carried out in the presence or absence of added solvents, such as aliphatic or aromatic hydrocarbons, eg. toluene, benzene or cyclohexane, alcohols, preferably in excess alcohol ROH I used for the acetylation, in particular n-butanol, higher fatty alcohols or glycols, ethers, eg. dibutyl ether, tetrahydrofuran or dioxane, or liquid, low molecular weight polyalkylene glycols, halogenated aliphatic or aromatic hydrocarbons, eg. chloroform, dichloromethane, chlorobenzene or dichlorobenzene, sulfoxides or sulfones, eg. dimethyl sulfoxide or sulfolane.

Instead of being carried out in these conventional solvents, the isomerization and acetalation of the adduct II to give the acetal IV and its conversion into n-butyraldehyde and/or n-butanol can also be effected in a phosphine melt. This procedure can advantageously be used in the case of phosphine-containing homogeneous catalysts. In principle, any desired phosphine can generally be chosen for the phosphine serving as a solvent, but the phosphine used in the melt is preferably that which serves as a ligand in the transition metal complex serving as the homogeneous catalyst.

If no further solvents are added in the conversion of the adduct II in reactions steps c) and d) in to the end products n-butyraldehyde and/or n-butanol, the reactants themselves, ie. the adduct II, the acetal IV, the alcohol ROH I and the water used according to the invention for hydrolyzing the acetal IV, as well as the end products of the reaction, dissolve the homogeneous catalysts used according to the invention.

The amount of alcohol ROH I added can be varied within wide ranges. The equimolar amount required for the formation of the acetal IV can, if desired, also be exceeded. For carrying out reaction step c), the alcohol ROH I is generally fed to the reactor in a molar ratio I/II of from 1:1 to 100:1, preferably from 1:1 to 10:1, in particular from 1:1 to 5:1, based on the adduct II used in this reaction step. A larger molar excess of the alcohol ROH I relative to the adduct II usually has no adverse effect on the result of the reaction in reaction steps c) and d), but the alcohol ROH I is advantageously used in the abovementioned ratios.

For the preparation of the end products n-butyraldehyde and n-butanol, water is added to the reaction mixture from reaction step c) in a molar ratio of in general from 1:1 to 100:1, preferably from 1:1 to 20:1, particularly preferably from 1:1 to 10:1, based on the adduct II which is fed to the reactor and which has been converted into the acetal intermediate IV in reaction step c) in the course of the novel process.

Since the presence of water has an adverse effect on the formation of the acetal IV from the adduct II and the alcohol ROH I in reaction step c), the reaction steps c) and d) are carried out in succession and the water is not added until reaction step d) is carried out. Reaction step c) is accordingly carried out under essentially anhydrous conditions, ie. in the absence of technically effective amounts of water. Of course, the presence of traces of water which have no measurable effect on yield and cost-efficiency of the novel process can be tolerated.

In the batchwise procedure, first the adduct II can be reacted with the alcohol ROH I in a reactor, for example a stirred kettle, under the stated conditions, to give the acetal IV and, after the end of the reaction, the reactants [sic] water can be passed into the resulting reaction mixture for further conversion of the acetal IV into n-butyraldehyde in reaction step d). The introduction of the water and its reaction with the acetal IV can be carried out in the same reactor as that used for reaction step c), ie. in a one-pot reaction; it is also possible to carry out reaction steps c) and d) in succession in different reactors. Similarly, in the continuous embodiment of the process, the water can be fed in a straight pass, for example in a tube or cascade reactor, into the reaction tube or a reactor of the reactor cascade, after expiry of the residence time required for the reaction in reaction step c), via a separate inlet.

If the desired end product is n-butanol, hydrogen in a molar ratio of in general from 1:1 to 100:1, preferably from 1:1 to 50:1, particularly preferably from 1:1 to 10:1, based on the adduct II fed to reaction step c), is also mixed with the reaction mixture from reaction step c), in addition to the water required for the hydrolysis of the acetal IV. In the batchwise process, this admixture can be effected by forcing the required amount of hydrogen into the reactor or by dispersing the hydrogen in the reaction medium, for example by means of bubble columns or by means of loop reactors equipped with jets for dispersing the hydrogen. The admixture of the hydrogen can be effected together with the water required for the combined hydrolysis/hydrogenation in reaction step d), as described above, after the reaction in reaction step c).

Since the hydrolysis of the acetal IV to n-butyraldehyde or the combined hydrolysis/hydrogenation of the acetal IV in reaction step d) can be carried out with the aid of the same catalyst as that used for the formation of the acetal IV from the adduct II, it is generally not necessary to work up the reaction mixture from reaction step c) before the addition of the reactants water or hydrogen and water, ie. before initiation of reaction step d).

If the desired end product is a mixture of n-butanol and n-butyraldehyde, the ratio of these products in the product mixture can be established, for example, through the addition of the hydrogen and/or the reaction temperature used. If substoichiometric amounts of hydrogen are used, it is clear that only a part of the starting material will be hydrogenated to n-butanol and, by using a lower reaction temperature, the rate of the hydrogenation reaction can be slowed down to such an extent that only a part of the starting material is hydrogenated to n-butanol.

After the end of the reaction, the reaction product is generally worked up by distillation, it being possible for the homogeneous catalyst used to be recovered from the bottom product of the distillation and, if desired, reused, for example by recycling the catalyst solution to reaction step c) involving the acetylation of the adduct II to the acetal IV and/or reaction step d), ie. its hydrolysis and, if required, hydrogenation. If recycling of the homogeneous catalyst in the novel process is desired, a solvent, preferably one which boils at a higher temperature than the reaction products n-butanol and n-butyraldehyde, may also advantageously be added to the reaction mixture. If the homogeneous catalyst used is chemically and thermally stable under the conditions of the distillation, the addition of a high-boiling solvent can be dispensed with and the homogeneous catalyst, for example in the form of a triphenylphosphine melt, can be recycled to the reaction.

In the working up by distillation, the reaction product n-butyraldehyde and/or n-butanol is furthermore separated from the alcohol ROH I liberated from the acetal IV by hydrolysis or hydrogenation or added in the preceding reaction steps c) and d), the amount of alcohol ROH I added for the acetalation advantageously being recycled to the first stage of the novel process, the addition reaction of the alcohol ROH I with 1,3-butadiene, and/or to reaction step c) of the novel process. The octanols or dodecanols formed as a result of the partial dimerization and trimerization of the butadiene, or the aldehydes corresponding to these alcohols, can be obtained as useful byproducts of the novel process, in the working up of the reaction product by distillation. Any incompletely converted acetal IV or any enol ether V isolated as a byproduct in the working up by distillation can be recycled to reaction steps c) or d).

In a further embodiment of the novel process, the isomerization and acetalation of the adduct II to the acetal IV and its hydrolysis or hydrogenation to n-butyraldehyde and/or n-butanol are carried out with the use of a heterogeneous catalyst in the liquid phase.

It has surprisingly been found that conventional heterogeneous hydrogenation catalysts which are essentially insoluble in the reaction medium may be used as catalysts both for the conversion of the adduct II into the acetal IV and for the hydrolysis of the acetal IV to n-butyraldehyde or for the combined hydrolysis/hydrogenation of the acetal IV to n-butanol. Among these hydrogenation catalysts, those which contain one or more elements of Group IA, VIA, VIIA or VIIIA, if necessary in combination with one or more elements of Group VA, of the Periodic Table of Elements, in particular chromium, molybdenum, tungsten, rhenium, ruthenium, cobalt, nickel, rhodium, iridium, osmium, palladium and/or platinum, if necessary in combination with iron and/or copper, are preferred.

Particularly active hydrogenation catalysts, such as nickel or the platinum metals, can advantageously be doped with main group elements which act as the catalyst poison and can be partially poisoned in this manner. As a result of this measure, it is possible to achieve a higher selectivity in the combined hydrolysis/hydrogenation of the acetal IV to n-butanol. Examples of main group elements suitable for the partial poisoning of such particularly active hydrogenation catalysts are the chalcogens, such as sulfur, selenium and tellurium, and the elements phosphorus, arsenic, antimony, bismuth, tin, lead and thalium. Subgroup elements suitable for this purpose are, for example, mercury and cadmium.

Heterogeneous catalysts which may be used in the novel process are, for example, precipitated catalysts. Such catalysts can be prepared by precipitating their catalytically active components from their salt solutions, in particular from the solutions of their nitrates and/or acetates, for example by addition of solutions of alkali metal and/or alkaline earth metal hydroxide and/or carbonate solutions [sic], as, for example, sparingly soluble hydroxides, hydrated oxides, basic salts or carbonates, then drying the resulting precipitates and subsequently calcining them at in general from 300 to 700° C., in particular from 400 to 600° C., to convert them into the relevant oxides, mixed oxides and/or mixed-valency oxides, which are reduced, for example, by treatment with reducing agents, such as hydrogen or hydrogen-containing gases, at, as a rule, from 50 to 700° C., in particular from 100 to 400° C., to give the relevant metals and/or to give oxidic compounds of low oxidation state and are converted into the actual, catalytically active form. As a rule, reduction is continued until no further water is formed. In the preparation of precipitated catalysts which contain a carrier, the precipitation of the catalytically active components may be effected in the presence of the relevant carrier. However, the catalytically active components can advantageously also be precipitated simultaneously with the carrier from the relevant salt solutions, as is the case, for example, in the precipitation of the catalytically active components by means of a water glass solution.

Hydrogenation catalysts which contain the metals or metal compounds catalyzing the hydrogenation as a deposit on a carrier are preferably used in the novel process. In addition to the abovementioned precipitated catalysts, which contain a carrier in addition to the catalytically active components, in general supported catalysts in which the catalytically active components have been applied to a carrier, for example, by impregnation are suitable for the novel process.

The method of application of the catalytically active metals to the carrier is as a rule not critical for the result of the process and can be effected in various ways. The catalytically active metals can be applied to these carriers, for example by impregnation with solutions or suspensions of the salts or oxides of relevant elements, drying and subsequent reduction of the metal compounds to give the relevant metals or oxidic compounds of low oxidation state by means of a reducing agent, preferably with the aid of hydrogen, hydrogen-containing gases or hydrazine. Another possibility for applying the catalytically active metals to these carriers comprises impregnating the carriers with solutions of salts which readily undergo thermal decomposition, for example with nitrates, or with complex compounds which readily undergo thermal decomposition, for example carbonyl or hydrido complexes of the catalytically active metals, and heating the carriers impregnated in this manner to 300–600° C. for thermal decomposition of the adsorbed metal compounds. This thermal decomposition is preferably carried out under an inert gas atmosphere. Suitable inert gases are, for example, nitrogen, carbon dioxide, hydrogen or the nobel gases. Furthermore, the catalytically active metals can be deposited on the catalyst carrier by vapor deposition or by flame spraying.

The content of the catalytically active metals in these supported catalysts is in principle not critical for the success of the novel process. It is clear to a person skilled in the art that higher contents of catalytically active metals in these supported catalysts lead to higher space-time yields than lower contents. In general, however, the supported catalysts used are those whose content of catalytically active metals is from 0.1 to 80, preferably from 0.5 to 30, % by weight, based on the total catalyst. Since these stated contents are based on the total catalyst, including carrier, but the different carriers have very different densities and specific surface areas, it is also possible to exceed or fall below these stated values without having any adverse effect on the result of the novel process. Of course, a plurality of the catalytically active metals may also be applied to the respective carrier. Furthermore, the catalytically active metals may be applied to the carrier by the processes of DE-A 2 519 817, EP-A 147 219 and EP-A 285 420. In the catalysts according to the abovementioned publications, the catalytically active metals are present as alloy [sic] which are produced by thermal treatment and/or reduction of the salts or complexes of the abovementioned metals, deposited on a carrier, for example, by impregnation.

The activation of the precipitated catalysts as well as of the supported catalysts can also be effected in situ in the reaction mixture by the hydrogen present there, but these catalysts are preferably activated before they are used in the novel process.

In general, the oxides of aluminum or of titanium, zirconium dioxide, silica, kieselguhr, silica gel, clays, for example montmorillonites, silicates, such as magnesium or aluminum silicates, zeolites, such as ZSM-5 or ZSM-10 zeolites, and active carbon may be used as carriers. Preferred carriers are aluminas, titanium dioxides, zirconium dioxide and active carbons. Mixtures of different carriers may of course also serve as carriers for catalysts which may be used in the novel process.

The following catalysts are examples of heterogeneous catalysts which may be used for carrying out reaction steps c) and d):

platinum dioxide, palladium on alumina, palladium on silica, palladium on barium sulfate, palladium on zirconium dioxide, rhodium on active carbon, rhodium on alumina, ruthenium on silica or active carbon, nickel on silica, cobalt on silica, cobalt on alumina, iron carbonyl powder, Raney rhenium, rhenium/palladium on active carbon, rhenium/platinum on active carbon, platinum oxide/rhodium oxide mixtures, platinum/palladium on active carbon, copper chromite, barium chromite, nickel/chromium oxide on alumina, cobalt sulfide, nickel sulfide, copper/molybdenum (VI) oxide/silica/alumina catalysts palladium, partially poisoned with selenium or lead, on active carbon catalysts and the catalysts according to DE-A 3 932 332, U.S. Pat. No. 3,449,445, EP-A 44444, EP-A 147 219, DE-A 3 904 083, DE-A 2 321 101, EP-A 415 202, DE-A 2 366 264 and EP-A 100 406.

In the novel process, hydrogenation catalysts which contain Brönsted and/or Lewis acids may also advantageously be used.

For example, the catalytically active metals themselves may act as Brönsted or Lewis acid centers if said metals are not completely reduced to the relevant metals with hydrogen or hydrogen-containing gases during the activation of the catalyst. This applies, for example, to the chromite-containing catalysts, such as copper chromite. Furthermore, such Lewis or Brönsted acid or basic centers can be introduced into the catalyst via the carrier used. Carriers containing Lewis or Brönsted acid centers are, for example, the aluminas, titanium dioxides, zirconium dioxide, silica, the silicates, clays, zeolites, mixed oxides of magnesium and of aluminum and active carbon.

Hydrogenation catalysts preferably used in the novel process are therefore supported catalysts which contain the elements of subgroups I, VI, VII and/or VIII of the Periodic Table of Elements, in particular the elements of subgroups VII and VIII of the Periodic Table of Elements, deposited on a carrier acting as a Brönsted or Lewis acid. Particularly advantageous catalysts are, for example, ruthenium on active carbon, ruthenium on alumina, ruthenium on silica, ruthenium on magnesium oxide, ruthenium on zirconium dioxide, ruthenium on titanium dioxide, palladium on alumina, palladium on silica, palladium on zirconium dioxide, palladium on barium sulfate and palladium, partially poisoned with selenium or lead, on active carbon catalysts.

Lewis or Brönsted acid components, such as zeolites, aluminas or silicas, phosphoric acid or sulfuric acid, can be added to hydrogenation catalysts which themselves have no such Brönsted or Lewis acid centers. They are generally added in amounts of from 0.01 to 5, preferably from 0.05 to 0.5, particularly preferably from 0.1 to 0.4, % by weight, based on the weight of the catalyst used.

Also suitable for the conversion of the adduct II into the acetal IV and its subsequent hydrolysis or combined hydrolysis/hydrogenation to n-butyraldehyde and/or n-butanol are heterogeneous catalysts which contain the complexes of transition metals of Groups VIA and VIIIA of the Periodic Table of Elements in heterogeneous form, for example those in which the relevant transition metal is fixed to a polymeric matrix, said complexes being capable of being used for the homogeneous catalysis of these reaction steps.

Such polymeric matrices may be resins, such as styrene/divinylbenzene resins or phenol/formaldehyde resins, to which the relevant ligands which serve for complexing the transition metal are preferably covalently bonded, which ligands in turn form complexes with the relevant transition metals and thus more or less immobilize them. Such heterogeneous, polymer-bound transition metal complex catalysts having 2,2'-bipyridine or 1,10-phenanthroline ligands or heterogeneous phosphine or phosphite complexes of the catalytically active transition metals can be prepared, for example, by the literature processes stated in the explanation of reaction step a) for the preparation of these catalysts.

With the stated heterogeneous catalysts, the acetalation of the adduct II to the acetal IV and subsequently its hydrolysis or hydrogenation to n-butyraldehyde and/or n-butanol can be carried out both continuously and batchwise.

The heterogeneous catalyst can be used either as a suspension in the liquid reaction medium or, preferably, arranged in a fixed bed or a plurality of fixed beds. With the use of a heterogeneous catalyst suspended in the liquid reaction medium, the process can be carried out, for example, in stirred kettles or loop reactors. When a heterogeneous catalyst arranged in a fixed bed is used, the reaction mixture is generally passed over the fixed catalyst bed by the liquid-phase or trickle-bed procedure.

Both the hydrolysis of the acetal IV and its combined hydrolysis and hydrogenation can be carried out in adiabatically or isothermally operated reactors. Here, the catalyst is generally loaded with the liquid reaction mixture at a space velocity of from 0.01 to 10, preferably from 0.02 to 3, particularly preferably from 0.03 to 1, kg of reaction mixture per l of catalyst per hour. When the heterogeneous catalysts are used, the reaction can be carried out in the presence or absence of a solvent. The solvents used may be the same solvents as those which may also be used in carrying out the process under homogeneous catalysis.

In the heterogeneous catalysis, too, the addition of the water required for reaction step d) has an adverse effect on the formation of the acetal IV from the adduct II and the alcohol ROH I in reaction step c). In the heterogeneous catalysis, too, the water is therefore not added until after the end of the reaction of reaction step c) and reaction step d) is initiated with the addition of the water or the addition of hydrogen and water. Accordingly, in the batchwise procedure under heterogeneous catalysis, the addition of water or the addition of hydrogen and water is effected in a manner similar to that described above for carrying out reaction steps c) and d) under homogeneous catalysis. In the continuous procedure with a straight pass, the [lacuna] for the preparation of n-butyraldehyde or the hydrogen and the water in the preparation of n-butanol are fed into the catalyst bed via separate inlets which are positioned so that the reaction in reaction step c) during the residence time of the reaction mixture over the catalyst bed is complete when the reaction mixture from reaction step c) comes into contact with the water or with the hydrogen and the water. Alternatively, a plurality of catalyst beds may also be arranged in the reactor or in a plurality of reactors connected in series, the reaction in reaction step c) being effected in the first catalyst bed or the first catalyst beds and the reaction in reaction step d) taking place, after the addition of water or the addition of hydrogen and water, in the downstream catalyst bed or the downstream catalyst beds.

Reaction step c) is consequently also carried out under heterogeneous catalysis under essentially anhydrous conditions, ie. in the absence of technically effective amounts of water. It is of course clear that the presence of traces of water which have no measurable effect on yield and cost-efficiency of the novel process can be tolerated.

The amount of the alcohol ROH I added for the production of the acetal IV from the adduct II can be varied within wide ranges also in the heterogeneous catalysis of reaction step c). The required equimolar amount can, if desired, also be exceeded. For carrying out reaction step c), the alcohol ROH I is generally fed to the reactor in a molar ratio I/II or from 1:1 to 100:1, preferably from 1:1 to 10:1, in particular from 1:1 to 5:1, based on the adduct II used in this reaction step. A larger molar excess, based on the adduct, of the alcohol generally does not have a disadvantageous effect on the result of the reaction in the reaction steps c) and d), but the alcohol ROH I is advantageously used in the abovementioned ratios. When the hydrolysis is carried out under heterogeneous catalysis, the water required in reaction step d) for liberating the n-butyraldehyde from the acetal IV produced in reaction step c) is added to the reaction mixture from reaction step c) in a molar ratio of in general from 1:1 to 100:1, preferably from 1:1 to 50:1, particularly preferably from 1:1 to 10:1, based on the amount of the adduct II fed beforehand to reaction step c). The amount of water added for the hydrolysis of the acetal IV in reaction step d) is advantageously based on the amount of the adduct II fed beforehand to reaction step c), since the discharge from reaction step c) is generally used without further working up for the reaction according to the reaction step. The combined isomerization and acetalation of the adduct II to give the acetal IV as well as its subsequent hydrolysis to n-butyraldehyde over the heterogeneous catalyst in the liquid phase is generally carried out at from 20 to 300° C., preferably from 50 to 280° C., particularly preferably from 80 to 250° C., and at in general from 1 to 100, preferably from 1 to 50, in particular from 2 to 10, bar.

In carrying out the process under heterogeneous catalysis, the hydrogen required in addition to water in the preparation of n-butanol in reaction step d) is added to the discharge from reaction step c) in a molar ratio in general from 1 to 100, preferably from 1.5 to 80, in particular from 2 to 40, based on the adduct II originally fed to reaction step c). The amount of hydrogen to be used in reaction step d) for the preparation of n-butanol is advantageously based on the amount of adduct II fed to reaction step c), since the discharge from reaction step c) is as a rule reacted without prior working up in reaction step d). The combined isomerization and acetalation of the adduct II to give the acetal IV and its subsequent hydrolysis/hydrogenation to n-butanol over the heterogeneous catalyst in the liquid phase is generally carried out at from 20 to 300° C., preferably from 50 to 280° C., particularly preferably from 80 to 250° C., and at in general from 1 to 300, preferably from 5 to 250, in particular from 20 to 200, bar. It is of course clear that the amounts of water and alcohol I required for the preparation of n-butanol and based on the adduct II are equal to the amounts of water and alcohol required for the preparation of n-butyraldehyde from the adduct II.

If the desired end product is a mixture of n-butyraldehyde and n-butanol, in general water, alcohol I and hydrogen are admixed, in a manner similar to that described above, in a ratio, based on the adduct II introduced in the reaction step c), which makes it possible to obtain both end products in the desired product ratio. In addition, the ratio of these two end products in the reactor discharge can also be controlled by means of the use of certain heterogeneous catalysts, for example by using heterogeneous catalysts which have high hydrolysis activity and relatively low hydrogenation activity compared therewith. For example, catalysts deactivated or partially poisoned with regard to their hydrogenation properties, for example palladium, partially poisoned with selenium or lead, on active carbon catalysts can advantageously be used for this purpose.

The liquid reaction discharge from reaction step d) is generally worked up by distillation, in a manner similar to that described for carrying out this reaction step with homogeneous catalysts. When heterogeneous catalysts are used, there is of course no recycling of the catalyst, as may be advantageous when homogeneous catalysts are used. The recycling of the alcohol ROH I liberated or added again in reaction step d) to the process stage involving the addition reaction of the alcohol ROH I with 1,3-butadiene and/or to the reaction in reaction step c) can advantageously be carried out in a manner similar to that described for the reaction in this reaction step with homogeneous catalysts.

As stated above, an advantage of the novel process is that the same heterogeneous catalyst can be used both for the combined isomerization/acetalation in reaction step c) and for the hydrolysis of the acetal IV to n-butyraldehyde or for the combined hydrolysis/hydrogenation of the acetal IV in reaction step d), with the result that catalyst costs can be reduced. Depending on the type of apparatus used for the preparation of n-butyraldehyde and/or n-butanol by the novel process, and furthermore depending on the desired composition of the end product of the novel process with respect to the butyraldehyde/butanol ratio, it may however also prove advantageous if different heterogeneous catalysts from among those to be used according to the invention are employed in the individual reaction steps c) and d).

Because reaction steps c) and d) are carried out in successive reaction stages, various modes of operation can be used in the individual process stages. For example, the conversion of the adduct II to the acetal IV can be effected alternatively under homogeneous catalysis or over heterogeneous catalysts, and the hydrolysis or the combined hydrolysis/hydrogenation of the acetal IV to give n-butyraldehyde and/or n-butanol can be effected alternatively in the liquid phase with the use of homogeneous catalysts or heterogeneous catalysts.

The alcohol ROH I liberated from the acetal IV in the hydrolysis or combined hydrolysis/hydrogenation is preferably recycled to the reaction in reaction step a) and/or to the reaction in reaction step c).

As stated above, instead of the butenyl ether II produced in the reaction steps a) and b) of the novel integrated process, a butenyl ether of the formula II prepared in another manner may also be used in reaction step c). The above statements on carrying out reaction steps c) and d) are of course entirely applicable when such a butenyl ether of the formula II prepared outside the integrated process in another manner is used as starting material in reaction step c). Such a procedure is advantageous when, at a production location, the butenyl ether of the formula II is available from another preparation process.

BRIEF DESCRIPTION OF THE DRAWINGS

The novel process is explained in more detail with reference to the flow diagram in the drawing, which schematically shows an advantageous embodiment of the novel process in which both the addition reaction of the alcohol ROH I with 1,3-butadiene or a butadiene-containing hydrocarbon mixture and the isomerization and acetylation of the adduct II to give the acetal IV and its hydrolysis or combined hydrolysis/hydrogenation to n-butyraldehyde and/or n-butanol are carried out in a single process stage in the liquid phase. Since this process flow diagram is intended to illustrate only the path of the starting material, intermediate and product streams in the novel process, for the sake of clarity obvious details of the plant, such as pumps, heat exchangers, valves or relays, were not drawn in the process flow diagram.

A mixture of 1,3-butadiene or a butadiene-containing hydrocarbon mixture and the alcohol ROH I, preferably n-butanol, is fed to the reactor 2 via the supply line 1 to be fed with 1,3-butadiene and the alcohol ROH I via the supply lines 3 and 4, respectively. The starting materials can of course also be fed to the reactor 2 via separate lines. In the reactor 2, the alcohol ROH I is subjected to an addition reaction catalytically, preferably by means of a Brönsted acid, in particular by means of an acidic cation exchanger, with 1,3-butadiene, in general a mixture of the starting materials II and III being formed. The reaction discharge from the reactor 2, which essentially consists of the adducts II and III, relatively high-boiling butadiene derivatives and unconverted 1,3-butadiene and alcohol ROH I, is fed via line 5, for example, to a gas/liquid separator 6, in which case gaseous 1,3-butadiene is separated by distillation from the liquid components of the reaction discharge of reactor 2 and are either recycled via the lines 7, 8 and 1 to the reactor 2 or fed via the lines 7 and 9 to the flare for combustion. The liquid mixture separated off in the column 6 is passed via line 10 to the distillation column 11, in which the more readily volatile adduct III is separated by distillation from the less volatile adduct II and from any alcohol ROH I and relatively high-boiling butadiene derivatives present. The adduct III, unconverted alcohol ROH I and any unconverted 1,3-butadiene present are then recycled via the lines 12 and 1 to the reactor 2, where the adduct III is isomerized in the presence of freshly introduced 1,3-butadiene and alcohol ROH I to give the adduct II. Alternatively, the unconverted alcohol ROH I can also be fed with the adduct II via the line 13 to the reactor 14. The low boilers, eg. vinylcyclohexene, fed with the reactor discharge from reactor 2 to the column 11 are fed, if desired together with the residual butadiene separated off in the column 11, via outlet 42 to the flare. Instead of a single distillation column 11, it is also possible to use a plurality of distillation columns connected in series for separating the liquid reaction discharge from reactor 2 by distillation. When a plurality of distillation columns are used instead of a single distillation column 11, relatively high-boiling reaction products contained in the discharge from reactor 2, if desired dibutyl ether, the alkoxyoctadienes or alkoxydodecatrienes, can be separated from the adduct II and removed from the process. Since these compounds do not have an adverse effect in the further process according to reaction steps c) and d), separation may also be omitted and dibutyl ether, the alkoxyoctadienes or alkoxydodecatrienes fed with the adduct II via the line 13 to the reactor 14.

The liquid discharge from column 11, which discharge has been freed from the more readily volatile adduct III and from low-boiling byproducts and any higher-boiling byproducts, is fed, if desired together with unconverted alcohol ROH I, via line 13 to the reactor 14, in which the adduct II is reacted with the alcohol ROH I recycled via line 43 or, if required, alcohol ROH I freshly added via line 15, preferably with the n-butanol recycled via line 43 or 15 or freshly added n-butanol, in the presence of a homogeneous or heterogeneous transition metal catalyst to give the acetal IV, and the latter is then hydrolyzed to n-butyraldehyde or converted in a combined hydrolysis/hydrogenation into n-butanol and, if desired, n-butyraldehyde. In the embodiment shown in the drawing, the reactor 14 is in the form of a tube reactor with a straight pass of the reaction mixture. The water and the hydrogen can be fed into the reactor via the feeds 17 and 18, which, as shown in the drawing, may be mounted at different heights on the reactor 14 or may also be at the same height. If n-butyraldehyde alone is to be produced in the plant, the hydrogen supply line 16 may remain closed or the amount of hydrogen required to improve the catalyst time on stream may be introduced via this line and, if desired, the line 16. If desired, carbon monoxide may also be passed into the reactor for this purpose together with the hydrogen.

The liquid reaction discharge from reactor 14, which essentially contains n-butyraldehyde and/or n-butanol, relatively high-boiling butadiene derivatives, for example octanols or dodecanols, unconverted water and possibly excess water and, if a homogeneous catalyst was used in the reactor 14, dissolved catalyst, is fed via line 19 to the distillation column 20. Hydrogen which may have been added via feed 18 for producing n-butanol and which is unconverted is for the most part removed from the reactor 14 via line 21 and either recycled via line 18 or 16 to the reactor 14 or flared.

In the distillation column 20, the reaction discharge from reactor 14 is separated into its components by distillation. The more readily volatile n-butyraldehyde is removed at the top via line 22, if desired together with low-boiling byproducts, and, if required, is fed, for further purification, to an additional distillation stage which is not shown in the drawing. Newly formed n-butanol is removed from the column via line 23 and fed via line 24 for further use. Higher-boiling products, for example dibutyl ether, octanols and dodecanols, can be removed via a plurality of outlets in the lower part of the column 20, which are represented by the outlet 26 in the drawing. If a homogeneous catalyst was used in the reactor 14, the catalyst solution is removed from the bottom of the column 20 via line 27 and, if necessary after removal of a part-stream of consumed catalyst, is recycled to the reactor 14 via line 28 and with addition of fresh catalyst solution via line 29.

If desired, the reaction in reactor 14 can be controlled so that either n-butyraldehyde alone or only n-butanol is produced there. If in such a case, for example, n-butanol alone is produced in reactor 14, n-butyraldehyde can, if desired, then be produced in a further embodiment of the novel process in a reactor 30 which is operated parallel to the reactor 14 and is supplied with a part-stream of the discharge of column 11 via line 31. As in reactor 14, in reactor 30, the adduct II is reacted with the alcohol I, preferably with n-butanol fed, for example, via lines 23, 25 and 44 or n-butanol fed via lines 37, 25 and 44 or fresh n-butanol fed in via line 33 until a steady-state operating condition of the plant has been established, to give the acetal IV and the latter is hydrolyzed to n-butyraldehyde but not hydrogenated to n-butanol. The water required for the hydrolysis is fed via the supply line 32 to the reactor 30, which in the drawing is designed as a tube reactor with a straight pass of the reaction mixture. The liquid discharge from reactor 30 passes via line 34 into the distillation column 35, from which n-butyraldehyde is removed via line 36. The n-butanol liberated from the acetal IV in the hydrolysis or the alcohol ROH I used instead of n-butanol in reactor 2 is removed from the column via line 37 and can be recycled via the lines 25 and 1 to the reactor 2, where it is again reacted with fresh 1,3-butadiene to give the adducts II and III or alternatively, after removal of water contained therein from the reaction in reactor 30 (not shown), can be recycled via the lines 25 and 44 to the reactor 30.

Higher-boiling products, for example, dimeric and trimeric butadiene derivatives, can be removed via a plurality of outlets, represented by outlet 38 in the drawing, in the lower part of the column 35. If a homogeneous catalyst was used in the reactor 30, the catalyst solution is advantageously recycled from the bottom of column 35 via line 39, if required after removal of a part-stream of spent catalyst, via line 40 and with addition of fresh catalyst solution via line 41, to the reactor 30.

In a preferred embodiment of the novel process, when n-butanol is used as alcohol ROH I, the n-butanol which is isolated in column 20 and removed via line 23 and which consists of the n-butanol newly formed from 1,3-butadiene and the n-butanol originally added via line 4 or 15 and n-butanol liberated again in the course of reaction step c) in reactor 14 is divided into two part-streams, the newly formed amount of n-butanol being fed via line 24 for further use and the amount of n-butanol originally used as alcohol ROH I being recycled via the lines 25 and 1 to the reactor 2, unless it is fed, as described above, via the lines 25 and 44 to any reactor 30 present and operated parallel to the reactor 14, or recycled via the lines 23 and 43 to the reactor 14. Depending on the design of the plant and the resulting demand, these butanol streams can be divided by means of distributors not shown in the drawing and present at the points of intersection of line 37 with line 25 and of line 25 with line 44 and at the point where the line 23 branches into the lines 24 and 25. Until a steady-state operating condition has been established on the plant, the reactors 14 and/or 30 may additionally be supplied with n-butanol via the lines 15 and 33, respectively.

When an alcohol ROH I other than n-butanol is used, depending on its boiling point it is removed from the column 20 via a separate outlet not shown on the drawing and is recycled to the reactor 2 via the lines 25 and 1 and/or to the reactor 14 or reactor 30 via the line 43 or 44, respectively.

The n-butanol removed from column 20 via line 23 and any alcohol ROH I removed via a separate outlet and differing from n-butanol are, before being further used or recycled to the reactors 2 and 14, subjected to a further distillative purification not shown in the drawing, in order to remove any impurities contained therein, such as dibutyl ether, and residual amounts of water from the reaction in reactor 14. The same applies to the further distillative purification of the higher-boiling products removed via outlet 26. The distillative purification of any alcohol ROH I removed via a separate outlet and of the n-butanol removed via line 23 and then recycled may be necessary in certain circumstances in order to avoid a build up of impurities and water in the process circulation. The distillative purification of the discharges from column 20 can be carried out by conventional distillation methods and does not form a subject of the present invention. The above statement applies correspondingly to the products removed from column 35 via the lines 36, 37 and 38. In this context, it is once again pointed out that the outlets from the columns 11, 20 and 35 are purely schematic in the drawing. The composition of the products to be distilled in these columns varies depending on the procedure used in the reactors 2, 14 and 30 and it is a routine task of a person skilled in the art appropriately to dimension the distillation column or distillation columns required for separating the products in accordance with the product composition present in each case.

By means of the novel processes, the end products n-butyraldehyde and n-butanol can be obtained, starting from 1,3-butadiene, with a higher selectivity than in the processes known to date, which use butadiene as the starting material for the preparation of these products.

EXAMPLES

Commercial 1,3-butadiene stabilized with 4-tert-butylpyrocatechol was used in the examples.

Example 1

(Reaction Step a)

A 0.3 l stirred autoclave was filled with 67.0 g (0.90 mol) of n-butanol and with 15.0 g of Lewatit® SPC 118 in the H$^+$ form, which had been washed beforehand with water and n-butanol. 47.9 g (0.88 mol) of 1,3-butadiene was then forced into the reactor. After a reaction time of 10 hours at 90° C. and 9 bar, a selectivity of 48.4% for 3-butoxybut-1-ene and a selectivity of 41.1% for 1-butoxybut-2-ene (based on butadiene) were found at a conversion of 46%.

Example 2

A 0.3 l stirred autoclave was filled with 67.0 g (0.90 mol) of n-butanol and with 11.5 g of Lewatit® SPC 118 in the H$^+$ form, which had been washed beforehand with water and n-butanol, and with 3.5 g of a Lewatit® SPC 118 ion exchanger doped with copper(II) chloride. 47.0 g (0.88 mol) of 1,3-butadiene were then forced into the autoclave. After reaction for 10 hours at 90° C. and under autogeneous pressure, a selectivity of 46.8% for 3-butoxybut-1-ene and a selectivity of 44.3% for 1-butoxybut-2-ene (based on butadiene) were obtained at a conversion of 69.1%.

Example 3

A heatable 1.4 l tube reactor was charged with 1 kg of a gel-like ion exchanger of the brand Amberlite® IR 120 in the H$^+$ form, washed with water and n-butanol. 1,3-Butadiene and n-butanol were mixed in the liquid phase at 20 bar upstream of the reactor and then passed continuously over the ion exchanger bed. The effect of the reaction parameters temperature, flow rate and 1,3-butadiene/n-butanol molar ratio was investigated within a wide range. The results obtained under the various experimental condition are shown in Table 1. The analysis of the product composition was carried out by means of calibrated gas chromatography (based on butadiene).

Example 4

Experimental series on the addition reaction of n-butanol with 1,3-butadiene under the reaction conditions stated in Tables 2, 3 and 4 were carried out in a 0.3 l stirred autoclave and the results shown in these tables were obtained. Table 2 relates to the use of different, acidic undoped ion exchangers as catalysts, Table 3 shows the results of experiments in which mixtures of different amounts of undoped Lewatit® SPC 118 ion exchanger with copper(II) chloride-doped Lewatit® SPC 118 ion exchanger were used as catalysts and Table 4 lists the results obtained with mixtures of ion exchangers, doped with various copper(II) salts, with the respective undoped ion exchangers as catalysts.

TABLE 1

Continuous addition reaction of n-butanol with butadiene

| Flow rate of | | Pres- | | | Selectivity [%] | | | | | |
|---|---|---|---|---|---|---|---|---|---|---|
| Butanol [g/h] | Butadiene [g/h] | sure [bar] | Temp. [° C.] | Conversion of butadiene [%] | 3-Butoxy-but-1-ene | 1-Butoxy-but-2-ene | Butoxy-octadiene | Remainder[1] | Total Oct.[2]/VCH[3] | unknown compounds |
| 81.5 | 46.0 | 20 | 91 | 65.1 | 40.5 | 36.4 | 11.5 | 4.5 | 1.9 | 5.2 |
| 83.9 | 39.2 | 20 | 80 | 39.3 | 51.0 | 36.8 | 8.6 | 0.8 | 2.0 | 0.8 |
| 49.0 | 26.2 | 20 | 80 | 57.0 | 49.2 | 37.7 | 9.5 | 1.1 | 1.4 | 1.1 |
| 59.1 | 18.9 | 20 | 80 | 49.9 | 52.1 | 39.1 | 6.6 | 0.4 | 1.0 | 0.8 |
| 49.0 | 13.5 | 20 | 80 | 72.0 | 50.0 | 40.1 | 7.1 | 0.7 | 1.0 | 1.1 |
| 147.9 | 44.5 | 20 | 111 | 72.4 | 42.2 | 43.3 | 8.1 | 1.5 | 1.7 | 3.2 |

Oct.[2] = Octatriene
VCH[3] = Vinylcyclohexene
Remainder[1]: Total of the compounds Butoxydodecatriene Dibutoxybutane Dibutoxyoctene Dodecatetraene

TABLE 2

Addition reaction of n-butanol with butadiene using acidic ion exchangers

| Ion exchanger | Butanol [mol] | Butadiene [mol] | Temp. [° C.] | Reaction time [h] | Conversion [%] | Selectivity [%] | | | | | |
|---|---|---|---|---|---|---|---|---|---|---|---|
| | | | | | | 3-Butoxy-but-1-ene | 1-Butoxy-but-2-ene | Butoxy-octadiene | Octatriene/VCH | Remainder | unidentified compounds |
| gel-like | | | | | | | | | | | |
| Lewatit ® S 100 | 0.90 | 0.88 | 100 | 6 | 17.6 | 35.6 | 39.9 | 3.3 | 12.6 | 0.2 | 8.5 |
| Lewatit ® SC 102 | 0.90 | 0.90 | 100 | 6 | 43.4 | 50.3 | 35.8 | 6.0 | 5.6 | 0.2 | 2.1 |
| Lewatit ® SC 104 | 0.90 | 0.87 | 100 | 6 | 49.9 | 49.4 | 37.5 | 7.0 | 3.7 | 0.4 | 2.1 |
| Dowex ® 50 W 4 | 0.90 | 0.88 | 100 | 6 | 45.2 | 50.9 | 37.8 | 2.7 | 6.2 | 0.0 | 2.4 |
| Amberlyst ® IRN 77 L | 0.90 | 0.97 | 110 | 6 | 66.4 | 41.3 | 36.8 | 9.3 | 2.4 | 0.9 | 9.0 |
| Amberlyst ® IRN 77 L | 0.90 | 0.91 | 100 | 6 | 71.3 | 42.2 | 36.8 | 9.6 | 2.4 | 1.2 | 7.7 |
| Amberlyst ® IRN 77 L | 0.90 | 0.43 | 100 | 6 | 63.8 | 46.4 | 39.9 | 1.4 | 2.3 | 0.2 | 9.7 |
| Amberlite ® IR 120 | 0.90 | 0.93 | 100 | 6 | 28.8 | 38.4 | 38.4 | 4.7 | 14.4 | 0.0 | 4.1 |
| Amberlite ® IR 132 E | 0.90 | 0.87 | 100 | 6 | 52.6 | 45.7 | 41.2 | 8.0 | 2.7 | 0.7 | 1.7 |
| macroporous | | | | | | | | | | | |
| Lewatit ® SPC 108 | 0.90 | 0.95 | 100 | 6 | 58.9 | 43.3 | 39.2 | 10.6 | 2.8 | 1.2 | 2.7 |
| Lewatit ® SPC 112 | 0.90 | 0.89 | 100 | 6 | 59.3 | 40.4 | 38.4 | 12.0 | 2.1 | 2.0 | 5.2 |
| Lewatit ® SPC 118 | 0.90 | 0.88 | 90 | 10 | 46.0 | 48.4 | 41.1 | 3.3 | 4.2 | 0.1 | 3.0 |
| Amberlyst ® 15 | 0.90 | 0.78 | 100 | 6 | 63.9 | 42.8 | 41.0 | 9.8 | 1.4 | 0.7 | 4.3 |
| Amberlite ® 200 | 0.90 | 0.88 | 100 | 6 | 64.3 | 44.8 | 39.5 | 6.9 | 4.5 | 0.4 | 3.9 |
| Amberlite ® 252 | 0.90 | 0.81 | 100 | 6 | 54.5 | 45.2 | 38.5 | 7.3 | 6.5 | 0.0 | 2.6 |
| Powder | | | | | | | | | | | |
| Bayer cat. K 1481 | 0.90 | 0.87 | 90 | 10 | 71.4 | 46.4 | 36.1 | 7.0 | 3.0 | 0.2 | 7.3 |

0.3 l autoclave: selectivity and Conversion based on butadiene
Remainder = Butoxydodecatrienes Dibutoxybutane Dodecatraene [sic]
Autogeneous pressure
15 g of ion exchanger in the H+ form

TABLE 3

Addition reaction of n-butanol with butadiene using CuCl₂-doped Lewatit ® SPC 118

| | | | | | | Selectivities [%] | | | | |
|---|---|---|---|---|---|---|---|---|---|---|
| H⁺-form [g] | CuCl₂-form [g] | Conversion [%] | 3-Butoxy-but-1-ene | 1-Butoxy-but-2-ene | Butoxyocta-dienes | Butoxy-dodecatrienes | Dibutoxy-butane | Octatriene/VCH | Dodecate-traene | unidentified compounds |
| 15.0 | 0.0 | 46.0 | 48.4 | 41.1 | 3.3 | 0.0 | 0.0 | 4.2 | 0.1 | 3.0 |
| 14.0 | 1.0 | 56.7 | 47.3 | 43.6 | 4.0 | 0.1 | 0.1 | 3.8 | 0.2 | 0.9 |
| 11.5 | 3.5 | 69.1 | 46.8 | 44.3 | 4.0 | 0.1 | 0.0 | 4.1 | 0.1 | 0.7 |
| 10.0 | 5.0 | 59.4 | 46.7 | 43.6 | 3.1 | 0.0 | 0.0 | 6.0 | 0.1 | 0.4 |
| 5.0 | 10.0 | 42.9 | 45.5 | 40.3 | 2.5 | 0.0 | 0.0 | 9.6 | 0.1 | 2.0 |
| 0.0 | 15.0 | 10.8 | 23.7 | 15.2 | 0.0 | 0.0 | 0.0 | 52.6 | 0.0 | 8.5 |

0.3 l autoclave: selectivity and conversion based on butadiene
Lewatit ® SPC 118 in the H⁺ or Cu form, washed with water and butanol
Autogeneous pressure, 90° C., 10 h reaction time
0.90 mol of butadiene
0.90 mol of butanol
Lewatit SPC 118

TABLE 4

Addition reaction of n-butanol with butadiene uskng CuX₂-doped ion exchangers

| 11.5 g of ion exchanger in the H form | 3.5 g of ion exchanger doped with CuX₂ | Conversion [%] | Selectivities [%] | | | | | | | |
|---|---|---|---|---|---|---|---|---|---|---|
| | | | 3-Butoxy-but-1-ene | 1-Butoxy-but-2-ene | Butoxy-octadienes | Butoxydo-decatrienes | Dibutoxy-butane | Octatriene/VCH | Dodeca-tetraene | unidentified compounds |
| Lewatit ® SPC 118 | CuCl₂ | 69.1 | 46.8 | 44.3 | 4.0 | 0.1 | 0.0 | 4.1 | 0.1 | 0.7 |
| | CuBr₂ | 65.1 | 47.7 | 45.0 | 3.8 | 0.0 | 0.0 | 2.8 | 0.1 | 0.4 |
| | CuSO₄ | 55.5 | 32.2 | 31.8 | 13.8 | 2.0 | 1.1 | 1.7 | 1.4 | 16.6 |
| | Cu(NO₃)₂ | 55.1 | 39.0 | 35.9 | 13.6 | 1.0 | 0.3 | 1.5 | 0.4 | 8.1 |
| | Cu(OAc)₂ | 59.7 | 34.1 | 33.2 | 15.0 | 1.7 | 1.1 | 0.9 | 1.2 | 12.9 |
| Lewatit ® SPC 108 | CuCl₂ | 61.5 | 36.8 | 33.8 | 13.8 | 0.7 | 0.1 | 0.9 | 0.0 | 13.9 |
| | CuBr₂ | 68.6 | 46.6 | 43.9 | 4.9 | 0.0 | 0.0 | 2.9 | 0.1 | 1.7 |
| Amberlyst ® R 15 | CuBr₂ | 63.5 | 37.0 | 35.1 | 14.8 | 0.9 | 0.5 | 1.1 | 1.2 | 9.5 |

0.3 l autoclave: selectivity and conversion based on butadiene
Autogeneous pressure, 90° C., 10 h reaction time
0.90 mol of butadiene
0.90 mol of butanol
Ion exchanger in the H or Cu form, washed with water and butanol
AcO: Acetate Example 5
(Isomerization of Adduct III to Give Adduct II)

A stirred autoclave was filled with 6.0 g of n-butanol, 2.0 g of 3-butoxybut-1-ene and 1.2 g of dried Lewatit® SPC 118 ion exchanger in the H⁺ form. The reaction mixture was heated to 105° C. and, after a reaction time of 2 and 6 hours, a sample was taken and the 3-butoxybut-1-ene/1-butoxybut-2-ene ratio was determined by gas chromatography. The change in this ratio with the reaction time is shown in Table 5.

TABLE 5

| Reaction time [h] | Molar ratio of | |
|---|---|---|
| | 3-butoxy-but-1-ene | 1-butoxy-but-2-ene |
| 0 | 100 | 0 |
| 2 | 70 | 30 |
| 6 | 61 | 39 |

Example 6

In the apparatus described in Example 3, 1,3-butadiene, n-butanol and a mixture of butoxybutenes as formed in the addition reaction of n-butanol with 1,3-butadiene and from which the major part of the 1-butoxy-2-ene [sic] had been removed beforehand by distillation were mixed in the liquid phase upstream of the reactor and then passed continuously at 20 bar and at various temperatures over the ion exchanger bed. The results of these experiments are listed in Table 6. All analyses were carried out by means of calibrated gas chromatography.

Example 7
(Comparison with Example 6)

Example 7 was carried out in the same way as Example 6, except that only 1,3-butadiene and n-butanol, but no butoxybutenes, were fed to the reactor. The results are listed in Table 6.

Comparison of the results of Examples 6 and 7 in Table 6 shows that, by recycling the undesired 3-butoxybut-1-ene formed in the addition reaction of n-butanol with 1,3-butadiene to the addition reaction, the further formation of this byproduct is suppressed.

TABLE 6

Continuous addition reaction of n-butanol with butadiene with recycling of 3-butoxybut-1-ene

| | Feed [g/h] | | | | | Conversion | Discharge [g/h] | | | | |
|---|---|---|---|---|---|---|---|---|---|---|---|
| | | | | | | | | | Total | | |
| Ex. | Butanol | Butadiene | 3-Butoxy-but-1-ene | 1-Butoxy but-2-ene | Temp. [° C.] | of buta-diene [%] | 3-Butoxy but-1-ene | 1-Butoxy but-2-ene | Butoxy octadienes | Oct.[2]/ VCH[3]) | unidentified compounds |
| 6 | 38.5 | 12.6 | 12.8 | 1.3 | 81 | 44.5 | 15.8 | 10.2 | 0.9 | 0.3 | 0.0 |
| 6 | 38.2 | 11.8 | 12.7 | 1.3 | 91 | 61.3 | 15.1 | 13.6 | 1.2 | 0.3 | 0.6 |
| 7 | 49.6 | 13.7 | — | — | 91 | 79.2 | 11.6 | 11.0 | 1.1 | 0.2 | 0.6 |

Oct.[2]= Octatriene
VCH[3]= Vinylcyclohexene

Example 8
Addition Reaction of n-butanol with 1,3-butadiene Under Zeolite Catalysis
a) Preparation of the $H^+$ form of the zeolites A commercial Y zeolite in the Na form (modulus: 5) was converted into the $H^+$ form as follows:

100 g of the zeolite were treated at 80° C. for ion exchange with ammonium sulfate solution, then washed with water, dried at 110° C. and calcined at 500° C. for five hours. This treatment was repeated once more. The resulting Y zeolite ($H^+$ form) still contained 0.02% by weight of sodium and its x-ray diffraction pattern corresponded to the typical x-ray diffraction pattern of a Y zeolite in the $H^+$ form (FAU-structure).

An Na zeolite which had been prepared according to Example 1 of U.S. Pat. No. 4,891,458 was treated in the same manner.

b) A 0.3 l stirred autoclave was filled with 67.0 g (0.90 mol) of n-butanol and with 5 g of the Y zeolite in the $H^+$ form, prepared according to Example 8a). 49.7 g (0.92 mol) of 1,3-butadiene were then forced in. After a reaction time of 6 hours at 130° C. and 9 bar, a selectivity of 32.4% for the formation of 3-butoxybut-1-ene and a selectivity of 20.3% for the formation of 1-butoxybut-2-ene were measured at a 1,3-butadiene conversion of 35.9%.

c) 0.90 mol of n-butanol and 0.88 mol of 1,3-butadiene were reacted in a manner similar to Example 8b) in the presence of 5 g of the zeolite in the $H^+$ form, prepared according to Example 8a). At a conversion of 40.0%, 3-butoxybut-1-ene was formed with a selectivity of 42.5% and 1-butoxybut-2-ene with a selectivity of 16.5%.

Example 9
Addition Reaction of n-butanol with Butadiene-containing Hydrocarbon Mixtures by Means of Proton Catalysis A 0.3 l stirred autoclave was filled with 51.0 g (0.69 mol) of n-butanol and with 10.0 g of Bayer catalyst ® K 2441 in the $H^+$ form. 40.0 g of a 1,3-butadiene-containing hydrocarbon mixture (15.4% of n-butane/isobutane, 45.4% of 1-butene/2-butene, 1.0% of isobutene, 38.2% of butadiene) were then forced into the autoclave. After a reaction time of 10 hours at 100° C. and 43 bar, the reaction was terminated and the reaction mixture was analyzed by gas chromatography:
Result:
Butadiene conversion: 18%
Isobutene conversion: 47%
1-butene/2-butene conversion: 4%
Selectivity of the formation of 3-butoxybut-1-ene: 41%
Selectivity of the formation of 1-butoxybut-2-ene: 46%
Selectivity of the formation of vinylcyclohexene: 9%

Example 10
Addition Reaction of n-butanol with 1,3-butadiene or Butadiene-containing Hydrocarbon Mixtures in the Presence of a Homogeneous Transition Metal Catalyst a) A 0.3 l stirred autoclave was filled with 74.0 g (1.0 mol) of n-butanol, 0.205 g (0.66 mmol) of palladium acetylacetonate and 2.02 g (7.3 mmol) of 1-(diisopropylphosphino)-3-(di-tert-butylphosphino) propane under a nitrogen atmosphere. 34.7 g (0.64 mol) of 1,3-butadiene were then forced in. After a reaction time of 20 hours at 80° C. and 9 bar, the reaction was terminated and the reaction mixture was analyzed by gas chromatography.

Result: Butadiene conversion: 88%
Selectivity of the formation of 3-butoxybut-1-ene: 64.5%
Selectivity of the formation of 1-butoxybut-2-ene: 34.3% b) A 0.3 l stirred autoclave was filled with 54.8 g (0.75 mol) of n-butanol, 0.122 g (0.4 mmol) of palladium acetylacetonate and 0.68 g (1.6 mmol) of 1,2-bis (dicyclohexylphosphino)ethane and 30 g of Mihagol under a nitrogen atmosphere. 26.0 g (0.48 mol) of 1,3-butadiene were then forced in. After a reaction time of 10 hours at 80° C. and 10 bar, the reaction was terminated and the reaction mixture was analyzed by gas chromatography.

Result: Butadiene conversion: 99%
Selectivity of the formation of 3-butoxybut-1-ene: 41.3%
Selectivity of the formation of 1-butoxybut-2-ene: 58.7% c) A 0.3 l stirred autoclave was filled with 54.8 g (0.75 mol) of n-butanol, 0.122 g (0.4 mmol) of palladium acetylacetonate and 0.34 g (0.8 mmol) of 1,2-bis (dicyclohexylphosphino)ethane under a nitrogen atmosphere. 25.9 g of a $C_4$ cut (52.9% of 1,3-butadiene, 22.3% of isobutene, 20.4% of 1-butene/2-butene, 4.4% of butane) were then forced in. After a reaction time of 10 hours at 70° C. and 11 bar, the reaction was terminated and the reaction mixture was analyzed by gas chromatography.

Result:
Butadiene conversion: 82%
Isobutene conversion: 0%
1-Butene/2-butene conversion: 0%
Selectivity of the formation of 3-butoxybut-1-ene: 48.3%
Selectivity of the formation of 1-butoxybut-2-ene: 48.3%

Example 11
(Conversion of the Adduct II into the Acetal IV)

A glass autoclave was filled with 0.022 g of the catalyst HRuCl(CO)(PPh$_3$)$_3$, 0.031 g of triphenylphosphine, 0.005 g of decanoic acid, 3.18 g (24.8 mmol) of 1-butoxybut-2-ene and 1.83 g (24.8 mmol) of n-butanol. After a reaction time of 16 hours at 160° C. under autogenous pressure, the reaction mixture was analyzed by means of calibrated gas chromatography. At a conversion rate of 85%, 1,1-dibutoxybutane was formed with a selectivity of 85.1% and 1-butoxybut-1-ene with a selectivity of 10.1%.

Example 12
(Hydrolysis of the Acetal IV to n-butyraldehyde Using a Homogeneous Catalyst)

A glass autoclave was filled with 3.0 g of water, 0.022 g of the catalyst HRuCl(CO)(PPh$_3$)$_3$, 0.031 g of triphenylphosphine, 0.005 g of decanoic acid and 3.0 g of 1,1-dibutoxybutane and stirred for 1 hour at 160° C. The reaction mixture was analyzed by means of calibrated gas chromatography. At a conversion of 90%, n-butyraldehyde was formed with a selectivity of 85%.

Example 13
(Conversion of the Adduct II into the Acetal IV and Hydrolysis of the Acetal IV to n-butyraldehyde in a Single Stage Using a Homogeneous Catalyst)

a) A glass autoclave was filled with 0.022 g of the catalyst HRuCl(CO)(PPh$_3$)$_3$, 0.031 g of triphenylphosphine, 0.005 g of decanoic acid, 3.18 g (24.8 mmol) of 1-butoxybut-2-ene and 1.83 g (24.8 mmol) of n-butanol and stirred for 8 hours under autogeneous pressure at 155° C. Thereafter, 2.2 g (122 mmol) of water were added and stirring was continued for a further hour at 155° C. The reaction mixture was analyzed by means of calibrated gas chromatography. At a conversion of 99%, n-butyraldehyde was obtained with a selectivity of 80% and 1,1-dibutoxybutane with a selectivity of 9%.

b) A glass autoclave was filled with 0.022 g of the catalyst HRuCl(CO)(PPh$_3$)$_3$, 0.031 g of triphenylphosphine, 0.005 g of decanoic acid, 3.18 g (24.8 mmol) of 1-butoxybut-2-ene, 1.83 g (24.8 mmol) of n-butanol and 2.2 g (122 mmol) of water and stirred for 16 hours under autogenous pressure at 155° C. The reaction mixture was analyzed by means of calibrated gas chromatography. At a conversion of 48%, n-butyraldehyde was obtained with a selectivity of 80%, 1-butoxybut-1-ene with a selectivity of 10% and 1,1-dibutoxybutane with a selectivity of 0.3%.

Example 14
(Combined Hydrolysis and Hydrogenation of the Acetal IV to n-butanol Using a Homogeneous Catalyst)

A glass autoclave was filled with 3.0 g of water, 0.022 g of the catalyst HRuCl(CO)(PPh$_3$)$_3$, 0.031 g of triphenylphosphine, 0.005 g of decanoic acid and 3.0 g of 1,1-dibutoxybutane and 10 bar hydrogen was then forced in. After a reaction time of 14 hours at 160° C., the reaction mixture was analyzed by means of calibrated gas chromatography. At a conversion of 99%, n-butanol was formed with a selectivity of 98.5%.

Example 15
(Acetalation of the Adduct II to Give the Acetal IV and Hydrogenation of the Acetal to n-butanol in a Single Stage Using a Homogeneous Catalyst)

A glass autoclave was filled with 0.022 g of the catalyst HRuCl(CO)(PPh$_3$)$_3$, 0.031 g of triphenylphosphine, 0.005 g of decanoic acid, 3.18 g (24.8 mmol) of 1-butoxybut-2-ene, 1.83 g (24.8 mmol) of n-butanol and 2.2 g (122 mmol) of water and 10 bar hydrogen was then forced in. After a reaction time of 16 hours at 155° C., the reaction mixture was analyzed by means of calibrated gas chromatography. At a conversion of 72%, n-butanol was formed with a selectivity of 65% and n-butyraldehyde with a selectivity of 20%.

Example 16
(Acetalation of the Adduct II to Give the Acetal IV Using a Heterogeneous Catalyst in the Liquid Phase)

A glass autoclave was filled with 0.10 g of the heterogeneous catalyst palladium on active carbon (10% by weight of Pd), 3.0 g (24 mmol) of 1-butoxybut-2-ene and 1.73 g (24 mmol) of n-butanol. After 16 hours at 150° C. under a hydrogen atmosphere (1 bar), the reaction mixture was analyzed by means of calibrated gas chromatography. At a conversion of 21%, 1,1-dibutoxybutane was formed with a selectivity of 42%, dibutyl ether with a selectivity of 25% and 1-butoxybut-1-ene with a selectivity of 22%.

We claim:

1. A process for the preparation of n-butyraldehyde and/or n-butanol, which comprises reacting a) 1,3-Butadiene or a butadiene-containing hydrocarbon mixture with an alcohol of the formula I

ROH                     I, where R is $C_2$–$C_{20}$-alkyl or alkenyl which is unsubstituted or substituted by 1 or 2 $C_1$–$C_{10}$-alkoxy or hydroxyl groups, or is $C_6$–$C_{10}$-aryl, $C_7$–$C_{11}$-aralkyl or methyl, at elevated temperatures and superatmospheric pressure in the presence of a Brönsted acid or in the presence of a complex of an element of Group Ia, VIIA or VIIIA of the Periodic Table of Elements with phosphorus- or nitrogen-containing ligands to give a mixture of the adducts of the formulae II

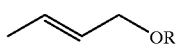

II and III

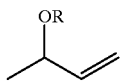

III b) isomerizing the adduct III to the adduct II, c) converting the adduct II into the acetal of the formula IV

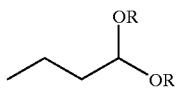

IV in the presence of an amount of an alcohol ROH I sufficient to form the acetal IV and of a homogeneous or heterogeneous transition metal catalyst which differs from dicobaltoctacarbonyl or hydridocobalttetracarbonyl, in the liquid phase, under essentially anhydrous conditions, and d) n-butyraldehyde and/or n-butanol are then produced from this acetal IV by reacting it, in the liquid phase, with hydrogen and water or water in the presence of a homogeneous or heterogeneous transition metal catalyst which differs from dicobaltoctacarbonyl or hydridocobalttetracarbonyl, and the alcohol ROH I is liberated
and the liberated alcohol ROH I is recycled to the reaction in reaction steps a) and/or c).

2. A process as claimed in claim 1, wherein the reaction of 1,3-butadiene or of a butadiene-containing hydrocarbon mixture with an alcohol ROH I is carried out in the presence of an acidic ion exchanger.

3. A process as claimed in claim 1, wherein the reaction of 1,3-butadiene or of a butadiene-containing hydrocarbon mixture with an alcohol ROH I is carried out in the presence of a catalyst comprising an alkyl, aryl or arylalkyl-phosphine complex of a transition metal from Group IA, VIIA or VIIIA of the Periodic Table of Elements.

4. A process as claimed in claim 1, wherein the reaction of 1,3-butadiene or of a butadiene-containing hydrocarbon mixture with an alcohol ROH I is carried out in the presence of a catalyst comprising an alkyl, aryl or arylalkyl-phosphine complex of rhodium, of nickel, of palladium, of iridium or of platinum.

5. A process as claimed in claim 1, wherein the isomerization of the adduct III to give the adduct II is carried out in the presence of a catalyst as used for the catalysis of the addition reaction of the alcohol ROH I with 1,3-butadiene or a butadiene-containing hydrocarbon mixture in reaction step a).

6. A process as claimed in claim 1, wherein the adduct III is separated from the adduct II, and the adduct III is then recycled to reaction step a) and is isomerized there to give the adduct II.

7. A process as claimed in claim 1, wherein the reaction steps c) and d) are carried out in succession in the liquid phase in the presence of a catalyst homogeneously soluble in the reaction medium.

8. A process as claimed in claim 1, wherein the reaction steps c) and d) are carried out in succession in the liquid phase in the presence of a catalyst which is homogeneously soluble in the reaction medium and is a monodentate or polydentate phosphine or phosphite complex of an element of Groups VIA and/or VIIIA of the Periodic Table of Elements.

9. A process as claimed in claim 1, wherein the reaction steps c) and d) are carried out in succession in the liquid phase in the presence of a catalyst which is homogeneously soluble in the reaction medium and comprises a phosphine or phosphite complex of an element of Group VIA and/or VIIIA of the Periodic Table of Elements and excess phosphine or phosphite ligands and reaction step d) is carried out in the presence of hydrogen and water and n-butanol is produced.

10. A process as claimed in claim 1, wherein the reaction steps c) and d) are carried out in succession in the liquid phase in the presence of a catalyst which is homogeneously soluble in the reaction medium and comprises a phosphine or phosphite complex of an element of the platinum metal group.

11. A process as claimed in claim 1, wherein the reaction steps c) and d) are carried out in succession in the liquid phase in the presence of a catalyst which is homogeneously soluble in the reaction medium and is a salt of an element of Group VIIIA of the Periodic Table of Elements.

12. A process as claimed in claim 1, wherein the reaction steps c) and d) are carried out in succession in the liquid phase in the presence of a catalyst which is homogeneously soluble in the reaction medium and is an aqua, amine, halo, cyano, carbonyl, amino and/or acetylacetonato complex of an element of Group VIA and/or Group VIIIA of the Periodic Table of Elements.

13. A process as claimed in claim 1, wherein the reaction steps c) and d) are carried out in the liquid phase in the presence of a catalyst which is homogeneously soluble in the reaction medium and is a salt or an aqua, amine, halo, cyano, amino and/or acetylacetonato complex of an element of Group VIA and/or VIIIA of the Periodic Table of Elements and reaction step d) is carried out in the presence of water and n-butyraldehyde is produced.

14. A process as claimed in claim 1, wherein the reaction steps c) and d) are carried out in succession in the liquid phase in the presence of a catalyst homogeneously soluble in the reaction medium and reaction step d) is carried out in the presence of hydrogen and water or water and the catalyst solution obtained after the products n-butyraldehyde and/or n-butanol have been separated off is reused for carrying out reaction steps c) and/or d).

15. A process as claimed in claim 1, wherein the reaction steps c) and d) are carried out in succession in the liquid phase in the presence of at least one heterogeneous catalyst essentially insoluble in the reaction medium.

16. A process as claimed in claim 1, wherein the reaction steps c) and d) are carried out in succession in the liquid phase in the presence of at least one heterogeneous catalyst which contains one or more elements of Groups IA, VIA, VIIA and/or VIIIA of the Periodic Table of Elements in the presence of absence of one or more elements of Group VA.

17. A process as claimed in claim 1, wherein the reaction steps c) and d) are carried out in succession in the liquid phase in the presence of at least one heterogeneous catalyst which contains one or more elements of Groups IA, VIA, VIIA and/or VIIIA of the Periodic Table of Elements in the presence or absence of one or more elements of Group VA and additionally a carrier.

18. A process as claimed in claim 1, wherein the reaction steps c) and d) are carried out in succession in the liquid phase in the presence of at least one heterogeneous catalyst which contains one or more elements of Groups IA, VIA, VIIA and/or VIIIA of the Periodic Table of Elements in the presence or absence of one or more elements of Group VA and additionally alumina, titanium dioxide, silica, zirconium dioxide, a silicate, a clay, a zeolite and/or active carbon as the carrier.

19. A process as claimed in claim 1, wherein the reaction steps c) and d) are carried out in succession in the liquid phase in the presence of at least one heterogeneous catalyst which contains palladium.

20. A process as claimed in claim 1, wherein the reaction steps c) and d) are carried out in succession in the liquid phase in the presence of at least one heterogeneous catalyst which is arranged in a fixed bed in each case.

21. A process as claimed in claim 1, wherein the reaction steps c) and d) are carried out in succession in the liquid phase in the presence of at least one heterogeneous catalyst which is arranged in from 2 to 5 fixed beds in each case.

22. A process as claimed in claim 1, wherein the reaction steps c) and d) are carried out in the liquid phase in succession using homogeneous and/or heterogeneous catalysts in the individual process stages.

23. A process as claimed in claim 1, wherein the alcohol ROH I used is n-butanol.

24. A process for the preparation of n-butyraldehyde and/or n-butanol, which comprises converting an ether of the formula II

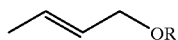

II where R is a $C_2$–$C_{20}$-alkyl or alkenyl group which is unsubstituted or substituted by 1 or 2 $C_1$–$C_{10}$-alkoxy or hydroxyl groups or is $C_6$–$C_{10}$-aryl or a $C_7$–$C_{11}$-aralkyl group or methyl, in the presence of an amount of an alcohol ROH I, where R has the abovementioned meanings, which is sufficient to form the acetal IV

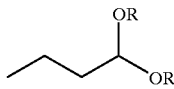

IV where R has the abovementioned meanings, and in the presence of a homogeneous or heterogeneous transition metal catalyst which differs from dicobaltoctacarbonyl or hydridocobalttetracarbonyl, in the liquid phase and under essentially anhydrous conditions, to give the acetal of the formula IV, and then producing n-butyraldehyde and/or n-butanol from this acetal IV by reacting it with hydrogen and water or water in the presence of a homogeneous or heterogeneous transition metal catalyst which differs from dicobaltoctacarbonyl or hydridocobalttetracarbonyl, in the liquid phase, and the alcohol ROH I is liberated again.

* * * * *